United States Patent
Root et al.

(10) Patent No.: US 7,115,091 B2
(45) Date of Patent: Oct. 3, 2006

(54) REUSABLE ENDOSCOPIC DEVICE AND RELATED SYSTEMS AND METHODS

(75) Inventors: Thomas V. Root, Beverly, MA (US); Robert J. Krupa, Leominster, MA (US)

(73) Assignee: Optim, Inc., Sturbridge, MA (US)

( * ) Notice: Subject to any disclaimer, the term of this patent is extended or adjusted under 35 U.S.C. 154(b) by 100 days.

(21) Appl. No.: 10/391,479

(22) Filed: Mar. 18, 2003

(65) Prior Publication Data
US 2004/0024290 A1    Feb. 5, 2004

Related U.S. Application Data

(60) Provisional application No. 60/365,310, filed on Mar. 18, 2002.

(51) Int. Cl.
| A61B 1/00 | (2006.01) |
| A61B 1/04 | (2006.01) |
| A61L 2/00 | (2006.01) |
| B01J 19/00 | (2006.01) |
| B32B 5/02 | (2006.01) |
| B32B 27/04 | (2006.01) |
| B32B 27/12 | (2006.01) |
| G05D 16/00 | (2006.01) |

(52) U.S. Cl. .................. 600/133; 422/25; 422/108; 422/112

(58) Field of Classification Search ........... 600/118, 600/133, 153–159; 422/3, 25–28, 105, 107, 422/108, 112–114
See application file for complete search history.

(56) References Cited

U.S. PATENT DOCUMENTS

| 3,963,438 | A | * | 6/1976 | Banez ................... 422/31 |
| 3,986,498 | A | * | 10/1976 | Lewis ................... 600/508 |
| 4,241,729 | A | * | 12/1980 | Aoshiro ................. 600/133 |
| 4,449,518 | A | * | 5/1984 | Konomura et al. ....... 600/133 |
| 4,457,334 | A | * | 7/1984 | Becker et al. ........... 137/461 |
| 4,527,551 | A | * | 7/1985 | Ishii ..................... 600/132 |
| 4,862,872 | A |  | 9/1989 | Yabe et al. |
| 4,919,113 | A |  | 4/1990 | Sakamoto et al. |
| 4,974,607 | A | * | 12/1990 | Miwa .................... 600/483 |
| 5,217,003 | A | * | 6/1993 | Wilk ..................... 600/109 |
| 5,359,993 | A | * | 11/1994 | Slater et al. ............ 600/133 |
| 5,368,015 | A | * | 11/1994 | Wilk ..................... 600/104 |
| 5,408,991 | A | * | 4/1995 | Iida et al. ............... 600/133 |
| 5,535,141 | A | * | 7/1996 | Lussi .................... 700/271 |
| 5,609,561 | A | * | 3/1997 | Uehara et al. ........... 600/112 |
| 5,634,880 | A | * | 6/1997 | Feldman et al. ......... 600/132 |
| 5,723,090 | A | * | 3/1998 | Beerstecher et al. ..... 422/26 |
| 5,732,401 | A | * | 3/1998 | Conway ................. 705/29 |
| 5,807,238 | A | * | 9/1998 | Feldman et al. ......... 600/133 |
| 5,868,667 | A | * | 2/1999 | Lin et al. ............... 600/133 |
| 5,984,875 | A | * | 11/1999 | Brune ................... 600/549 |
| 6,092,722 | A | * | 7/2000 | Heinrichs et al. ....... 235/375 |
| 6,193,510 | B1 |  | 2/2001 | Tsimerman |
| 6,240,312 | B1 | * | 5/2001 | Alfano et al. ........... 600/476 |
| 6,366,206 | B1 | * | 4/2002 | Ishikawa et al. ........ 340/573.1 |
| 6,408,682 | B1 | * | 6/2002 | Greszler ................. 73/40 |

(Continued)

*Primary Examiner*—John Leubecker
*Assistant Examiner*—Phillip R Smith
(74) *Attorney, Agent, or Firm*—Proskauer Rose LLP

(57) ABSTRACT

Reusable instruments, such as reusable medical instruments, and related systems and methods, are disclosed. In some embodiments, the reusable instrument can be an endoscope, which can be cleaned by sterilization. In certain embodiments, a method of sterilizing includes sterilizing the endoscope or portion thereof in a sterilization chamber while maintaining a pressure differential between the interior and exterior of the endoscope.

10 Claims, 11 Drawing Sheets

U.S. PATENT DOCUMENTS

| | | | |
|---|---|---|---|
| 6,436,032 B1 * | 8/2002 | Eto et al. | 600/117 |
| 6,452,624 B1 * | 9/2002 | Aloy | 348/71 |
| 6,461,295 B1 * | 10/2002 | Takada | 600/155 |
| 6,485,684 B1 | 11/2002 | Mapson et al. | |
| 6,712,756 B1 * | 3/2004 | Kura et al. | 600/118 |
| 6,712,760 B1 * | 3/2004 | Sano et al. | 600/160 |
| 6,726,620 B1 * | 4/2004 | Shibata et al. | 600/118 |
| 6,814,932 B1 | 11/2004 | Hlebovy et al. | |
| 6,884,392 B1 | 4/2005 | Malkin et al. | |
| 2001/0033807 A1 | 10/2001 | Lin et al. | |
| 2001/0041825 A1 * | 11/2001 | Shibata et al. | 600/118 |
| 2002/0013510 A1 * | 1/2002 | Moriyama | 600/118 |
| 2003/0109837 A1 * | 6/2003 | McBride-Sakal | 604/267 |
| 2004/0041031 A1 | 3/2004 | Root et al. | |
| 2004/0049172 A1 | 3/2004 | Root et al. | |
| 2004/0052679 A1 | 3/2004 | Root et al. | |

* cited by examiner

REUSABLE ENDOSCOPIC DEVICE AND RELATED SYSTEMS AND METHODS

CROSS-REFERENCE TO RELATED APPLICATION

The present application claims priority under 35 U.S.C. §119(e)(1) to U.S. Provisional Patent Application Ser. No. 60/365,310, filed on Mar. 18, 2002, and entitled "Endoscope and Autoclave System for Endoscope Sterilization," the contents of which are hereby incorporated by reference.

TECHNICAL FIELD

The invention relates to reusable instruments, such as endoscopes, and related systems and methods.

BACKGROUND

Endoscopes are commonly used to view a region inside a subject (e.g., a human, an animal), such as, for example, when performing a therapeutic or interventional medical procedure to remove a polyp within the intestine, when performing a diagnostic medical procedure to view the bronchii searching for tumors, or when performing a diagnostic medical procedure to ultrasonically image an organ (e.g., in transesophageal ultrasonic imaging). Typically, an endoscope has a manipulation portion coupled to an elongated portion (e.g., a flexible elongated portion, a rigid elongated portion, a semi-rigid elongated portion) so that, during use of the endoscope, the manipulation portion remains outside the subject while the elongated portion is at least partially disposed inside the subject. Generally, the elongated portion has one or more optical components (e.g., one or more lenses, imaging fiber optics, video imager) to illuminate and view the region inside the subject, and the manipulation portion has one or more devices designed to control the optical components and the position of the elongated portion in the subject. Optionally, the elongated portion can include one or more medical tools configured to perform a medical procedure on the subject. In general, after each use in a medical procedure, the endoscope is cleaned to remove detritus, and subsequently disinfected and/or sterilized.

SUMMARY

In one aspect, the invention features a method of charging a client for use of a reusable instrument (e.g., a reusable medical instrument, such as an endoscope). The method includes charging the client for use of the reusable instrument, where the charge to the client is at least partially based on the number of times the client has used the reusable instrument since last being charged for use of the reusable instrument.

In another aspect, the invention features a method of charging a client for use of a reusable instrument (e.g., a reusable medical instrument, such as an endoscope). The method includes reading recognition data from the reusable instrument to determine the identity of the reusable instrument, and determining the client based on the identity of the reusable instrument. The method also includes charging the client based on data associated with the client.

In a further aspect, the invention features a method of managing a condition of a reusable instrument (e.g., a reusable medical instrument, such as an endoscope). The method includes determining the identity of the reusable instrument, and determining, based on the identity of the reusable instrument, the number of times the reusable instrument has been used since the reusable instrument last underwent a maintenance procedure.

In one aspect, the invention features a method of maintaining a supply material associated with uses of a reusable instrument (e.g., a reusable medical instrument, such as an endoscope). The method includes determining the identity of the reusable instrument, and determining, based on the identity of the reusable instrument, the number of times the reusable instrument has been used since the supply material was last acquired by a client associated with the reusable instrument.

In another aspect, the invention features a method of preventing use of a reusable instrument (e.g., a reusable medical instrument, such as an endoscope). The method includes determining a client associated with the reusable instrument based on the identity of the reusable instrument, and preventing the reusable instrument from being used in a procedure based on data associated with the client.

In a further aspect, the invention features a method of maintaining a database for a reusable instrument (e.g., a reusable medical instrument, such as an endoscope). The method includes determining, each time the reusable instrument has been used in a procedure, that the reusable instrument has been used in a procedure, and updating, each time the reusable instrument has been used in a procedure, the database to indicate that the reusable instrument has been used in another procedure.

In one aspect, the invention features a method of charging a client. The method includes charging the client, where the charge to the client is at least partially based on a number of times the client has treated a reusable instrument (e.g., a reusable medical instrument, such as an endoscope) since last being charged.

In another aspect, the invention features a computer program product residing on a computer readable medium having a plurality of instructions stored thereon which, when executed by one or more processors, cause the one or more processors to cause a process to occur. The process includes charging a client for use of a reusable instrument (e.g., a reusable medical instrument, such as an endoscope), where the charge to the client is at least partially based on a number of times the client has used the reusable instrument since last being charged for use of the reusable instrument.

In a further aspect, the invention features a computer program product residing on a computer readable medium having a plurality of instructions stored thereon which, when executed by one or more processors, cause the one or more processors to cause the occurrence of a process. The process includes reading recognition data from a reusable instrument (e.g., a reusable medical instrument, such as an endoscope) to determine an identity of the reusable instrument, and determining a client associated with the reusable instrument based on the identity of the reusable instrument. The process also includes charging the client based on data associated with the client.

In one aspect, the invention features a computer program product residing on a computer readable medium having a plurality of instructions stored thereon which, when executed by one or more processors, cause the one or more processors to cause the occurrence of a process. The process includes determining an identity of the reusable instrument (e.g., a reusable medical instrument, such as an endoscope), and determining, based on the identity of the reusable instrument, a number of times the reusable instrument has been used since the reusable instrument last underwent a maintenance procedure.

In another aspect, the invention features a computer program product residing on a computer readable medium having a plurality of instructions stored thereon which, when executed by one or more processors, cause the one or more processors to cause the occurrence of a process. The process includes determining an identity of a reusable instrument (e.g., a reusable medical instrument, such as an endoscope), and determining, based on the identity of the reusable instrument, a number of times the reusable instrument has been used since the supply material was last acquired by a client associated with the reusable instrument.

In a further aspect, the invention features a computer program product residing on a computer readable medium having a plurality of instructions stored thereon which, when executed by one or more processors, cause the one or more processors to cause the occurrence of a process. The process includes determining an account for a client based on an identity of a reusable instrument (e.g., a reusable medical instrument, such as an endoscope), and preventing the client from using the reusable instrument in a procedure based on data associated with the client.

In one aspect, the invention features a computer program product residing on a computer readable medium having a plurality of instructions stored thereon which, when executed by one or more processors, cause the one or more processors to cause the occurrence of a process. The process includes determining, each time a reusable instrument (e.g., a reusable medical instrument, such as an endoscope) has been used in a procedure, that the reusable instrument has been used in a procedure, and updating, each time the reusable instrument has been used in a procedure, the database to indicate that the reusable instrument has been used in another procedure.

In another aspect, the invention features a computer program product residing on a computer readable medium having a plurality of instructions stored thereon which, when executed by one or more processors, cause the one or more processors to cause the occurrence of a process. The process includes charging a client, where the charge to the client is at least partially based on a number of times the client has treated a reusable instrument (e.g., a reusable medical instrument, such as an endoscope) since last being charged.

In a further aspect, the invention features a reusable instrument (e.g., a reusable medical instrument, such as an endoscope). The instrument includes an instrument body, and an indicator configured to provide the identity of the instrument. The indicator is integral with the instrument body, disposed on the exterior of the instrument body, or disposed in the interior of the instrument body.

In one aspect, the invention features a system that includes a reusable instrument (e.g., a reusable medical instrument, such as an endoscope) and a data recognition device. The instrument includes an instrument body and an indicator. The indicator is integral with the instrument body, disposed on the exterior of the instrument body, or disposed in the interior of the instrument body. The data recognition device is configured to read data from the indicator to determine the identity of the reusable instrument.

In another aspect, the invention features a reusable instrument (e.g., a reusable medical instrument, such as an endoscope) that includes an instrument body and an indicator. The indicator is integral with the instrument body, disposed on the exterior of the instrument body, or disposed in the interior of the instrument body. The indicator is configured to provide a serial number of the reusable instrument device, a product number of the reusable instrument, a treatment status of the reusable instrument, a procedure enablement status (e.g., a medical procedure enablement status) of the reusable instrument, or a supply status of the reusable instrument.

In a further aspect, the invention features a system that includes a reusable instrument (e.g., a reusable medical instrument, such as an endoscope) and a data recognition device. The instrument includes an instrument body and an indicator. The indicator is integral with the instrument body, disposed on the exterior of the instrument body, or disposed in the interior of the instrument body. The data recognition device is configured to read data from the indicator, where the data is a serial number of the reusable instrument, a product number of the endoscopic device, a treatment status of the reusable instrument, or a procedure enablement status of the reusable instrument.

In one aspect, the invention features a system that includes an article and a data recognition device. The article is a component of a treatment system (e.g., a sterilization system, a disinfection system) for the reusable instrument (e.g., a reusable medical instrument, such as an endoscope), a holder for a reusable instrument (e.g., a reusable medical instrument, such as an endoscope) that is configured to be removably housed in a treatment chamber (e.g., a reusable medical instrument, such as an endoscope) for the reusable instrument, or a docking station for a holder for a reusable instrument that is configured to be removably housed within a treatment chamber for the reusable instrument. The data recognition is integral with the article, disposed on an exterior of the article, or disposed in an interior of the article. The data recognition device is configured to read data from the reusable instrument to recognize a serial number of the reusable instrument, a product number of the reusable instrument, a treatment status of the endoscope, or a procedure enablement status of the reusable instrument.

In another aspect, the invention features a system that includes an article and a disabling device coupled to the article. The article is a component for a treatment system (e.g., a sterilization system, a disinfection system) for the reusable instrument (e.g., a reusable medical instrument, such as an endoscope), a holder for a reusable instrument (e.g., a reusable medical instrument, such as an endoscope) that is configured to be removably housed in a treatment chamber for the reusable instrument, or a docking station for a holder for a reusable instrument (e.g., a reusable medical instrument, such as an endoscope) that is configured to be removably housed within a treatment chamber for the reusable instrument. The disabling device is configured to change a procedure enablement status of a reusable instrument to prevent the reusable instrument from being used in a procedure.

In a further aspect, the invention features a system that includes an article and a treatment status device coupled to the article. The article is a component for a treatment system (e.g., a sterilization system, a disinfection system) for the reusable instrument (e.g., a reusable medical instrument, such as an endoscope), a holder for a reusable instrument (e.g., a reusable medical instrument, such as an endoscope) that is configured to be removably housed in a treatment chamber for the reusable instrument, or a docking station for a holder for a reusable instrument (e.g., a reusable medical instrument, such as an endoscope) that is configured to be removably housed within a treatment chamber for the reusable instrument. The treatment status device is configured to change a treatment status of a reusable instrument to indicate that the reusable instrument has been treated since it was last used in a procedure.

In one aspect, the invention features a method that includes reading data from a reusable instrument (e.g., a reusable medical instrument, such as an endoscope) to determine the identity of the reusable instrument.

In another aspect, the invention features a method that includes reading recognition data from a reusable instrument (e.g., a reusable medical instrument, such as an endoscope), where the recognition data is a serial number of the reusable instrument, a product number of the reusable instrument, a treatment status of the reusable instrument, a supply status of the reusable instrument, or a procedure enablement status of the reusable instrument (e.g., a medical procedure enablement status of the reusable instrument).

In a further aspect, the invention features a computer program product residing on a computer readable medium having a plurality of instructions stored thereon which, when executed by one or more processors, cause the one or more processors to cause the occurrence of a process. The process includes reading data from a reusable instrument (e.g., a reusable medical instrument, such as an endoscope) to determine the identity of the reusable instrument.

In one aspect, the invention features a computer program product residing on a computer readable medium having a plurality of instructions stored thereon which, when executed by one or more processors, cause the one or more processors to cause the occurrence of a process. The process includes reading recognition data from a reusable instrument (e.g., a reusable medical instrument, such as an endoscope), where the recognition data is a serial number of the reusable instrument, a product number of the reusable instrument, a treatment status of the reusable instrument, a supply status of the reusable instrument, or a procedure enablement status of the reusable instrument.

In another aspect, the invention features an endoscopic device that includes an endoscope body and a communication device. The communication device is integral with the endoscope body, disposed on the exterior of the endoscope body, or disposed in the interior of the endoscope body. The communication device is a wireless transmitter and/or a wireless receiver.

In a further aspect, the invention features a system that includes an endoscope body and a first communication device that is integral with the endoscope body, disposed on the exterior of the endoscope body, or disposed in the interior of the endoscope body. The system also includes a second communication device. The first communication device is a wireless transmitter and/or a wireless receiver, and the first and second communication devices are configured to wirelessly transmit data therebetween.

In one aspect, the invention features a method of communicating that includes wirelessly communicating data between an endoscope and an article.

In another aspect, the invention features a computer program product residing on a computer readable medium having a plurality of instructions stored thereon which, when executed by one or more processors, cause the one or more processors to cause the occurrence of a process. The process includes wirelessly communicating data between an endoscope and an article.

In a further aspect, the invention features a system that includes a treatment chamber (e.g., a sterilization chamber, a disinfection chamber) for treating a reusable instrument (e.g., a reusable medical instrument, such as an endoscope) and a cleaning device coupled to the treatment chamber so that, when the reusable instrument is disposed in the treatment chamber, the cleaning device is capable of interacting with an interior channel of the reusable instrument to at least partially clean the interior channel.

In one aspect, the invention features a system that includes a treatment chamber (e.g. a sterilization chamber, a disinfection chamber) for treating a reusable instrument (e.g., a reusable medical instrument, such as an endoscope) and a cleaning device coupled to the treatment chamber so that, when the reusable instrument is disposed in the treatment chamber, the cleaning device interacts with an exterior surface of the reusable instrument to at least partially clean the exterior surface of the reusable instrument.

In another aspect, the invention features a system that includes a treatment chamber (e.g., a sterilization chamber, a disinfection chamber) for treating a reusable instrument (e.g., a reusable medical instrument, such as an endoscope) and a fluid source coupled to the treatment chamber so that, when the reusable instrument is disposed in the treatment chamber, the fluid source is adjacent an opening in an interior channel of the reusable instrument so that the fluid source can dispose a fluid into an interior channel of the reusable instrument.

In a further aspect, the invention features a system that includes a sterilization chamber and a first cleaning device coupled to the sterilization chamber so that, when an endoscope is disposed in the sterilization chamber, the first cleaning device is capable of interacting with an interior channel of the endoscope to at least partially clean the interior channel. The first cleaning device is, for example, a brush, a fluid emission device, a radiation emission device, a pipe cleaner, a thread, or a rope. The system also includes a controller configured to control a position of the first cleaning device within the sterilization chamber so that the first cleaning device can be moved from a first position in the sterilization chamber to a second position in the sterilization chamber that is different from the first position, where the first cleaning device is at least partially disposed within the interior channel of the endoscope when in the second position. The system further includes a second cleaning device coupled to the sterilization chamber so that, when the endoscope is disposed in the sterilization chamber, the second cleaning device interacts with an exterior surface of the endoscope to at least partially clean the exterior surface of the endoscope. The cleaning device is, for example, a brush a fluid emission device, a radiation emission device, a pipe cleaner, a thread, or a rope. The system also includes a controller configured to control a position of the second cleaning device within the sterilization chamber so that the second cleaning device can be moved from a first position in the sterilization chamber to a second position in the sterilization chamber that is different from the first position, where the second cleaning device is adjacent the exterior surface of the endoscope when in the second position. The system further includes a fluid source coupled to the sterilization chamber so that, when the endoscope is disposed in the sterilization chamber, the fluid source can dispose a fluid into the interior channel of the endoscope. The fluid source is, for example, a fluid emission device. The system also includes a controller configured to control a position of the fluid source within the sterilization chamber so that the fluid source can be moved from a first position in the sterilization chamber to a second position in the sterilization chamber that is different from the first position, where the fluid source is adjacent an opening in the interior channel of the endoscope when in the second position.

In one aspect, the invention features a method of cleaning an interior channel of a reusable instrument (e.g., a reusable medical instrument, such as an endoscope). The method includes disposing the reusable instrument in a treatment chamber, and at least partially disposing a cleaning device within the interior channel of the reusable instrument to clean the interior channel of the reusable instrument.

In another aspect, the invention features a method of cleaning an exterior surface of a reusable instrument (e.g., a reusable medical instrument). The method includes disposing the reusable instrument in a treatment chamber (e.g., a sterilization chamber, a disinfection chamber), and disposing a cleaning device adjacent an exterior surface of the reusable instrument to remove contaminants from the exterior surface of the reusable instrument.

In a further aspect, the invention features a method of cleaning an interior channel of a reusable instrument (e.g., a reusable medical instrument, such as an endoscope). The method includes disposing the reusable instrument in a treatment chamber (e.g., a sterilization chamber, a disinfection chamber), and disposing a fluid in an interior channel of the reusable instrument to clean the interior channel.

In one aspect, the invention features a computer program product residing on a computer readable medium having a plurality of instructions stored thereon which, when executed by one or more processors, cause the one or more processors to cause the occurrence of a process. The process includes disposing a reusable instrument (e.g., a reusable medical instrument, such as an endoscope) in a treatment chamber (e.g., a sterilization chamber, a disinfection chamber), and at least partially disposing a cleaning device within the interior channel of the reusable instrument to clean the interior channel of the reusable instrument.

In another aspect, the invention features a computer program product residing on a computer readable medium having a plurality of instructions stored thereon which, when executed by one or more processors, cause the one or more processors to cause the occurrence of a process. The process includes disposing a reusable instrument (e.g., a reusable medical instrument, such as an endoscope) in a treatment chamber (e.g., a sterilization chamber, a disinfection chamber), and disposing a cleaning device adjacent an exterior surface of the reusable instrument to remove contaminants from the exterior surface of the reusable instrument.

In a further aspect, the invention features a computer program product residing on a computer readable medium having a plurality of instructions stored thereon which, when executed by one or more processors, cause the one or more processors to cause the occurrence of a process. The process includes disposing a reusable instrument (e.g., a reusable medical instrument, such as an endoscope) in a treatment chamber (e.g., a sterilization chamber, a disinfection chamber), and disposing a fluid into an interior channel of the reusable instrument to clean the interior channel.

In one aspect, the invention features an endoscopic device that includes an endoscope body and a light source. The endoscope body includes an elongated portion having a proximal end, a distal end, and a longitudinal channel extending from the proximal end to the distal end, where the longitudinal channel is sealed at the distal end. The endoscope body also includes a manipulation portion having an interior, where the manipulation portion is coupled to the proximal end of the elongated portion. The light source is disposed in the interior of the manipulation portion. The light source is in optical communication with the distal end of the elongated portion through the longitudinal channel.

In another aspect, the invention features an endoscopic device that includes an endoscope body and a pressure regulator. The endoscope body has an interior, an exterior, and an opening capable of allowing fluid communication between the interior and exterior. The pressure regulator is coupled to the opening in the endoscope body so that the pressure regulator is capable of regulating fluid communication between the interior of the endoscope and the exterior of the endoscope.

In a further aspect, the invention features a system that includes an endoscope body and a pressure regulator. The endoscope body has an interior, an exterior, and an opening capable of allowing fluid communication between the interior and exterior. Tile pressure regulator is coupled to the opening in the endoscope. The system also includes a gas source coupled to the pressure regulator. The pressure regulator and the gas source are configured so that the pressure gas source is capable of regulating fluid communication between the gas source and the interior of the endoscope body. The gas source is capable of removing gas from the interior of the endoscope body or adding gas to the interior of the endoscope body.

In one aspect, the invention features a method of operating an endoscope. The endoscope has a proximal end, a distal end and a longitudinal channel extending from the proximal end to the distal end. The method includes generating light in the proximal end of the endoscope, and transmitting the light generated in the proximal end of the endoscope to the distal end of the endoscope through the longitudinal channel.

In another aspect, the invention features a method of sterilizing an endoscope. The endoscope has an interior, an exterior, and a distal end. The method includes sterilizing a portion of the interior of the endoscope while maintaining a pressure differential between the interior of the endoscope and the exterior of the endoscope of at most about five psi. The portion of the interior of the endoscope is sealed at the distal end of the endoscope.

In a further aspect, the invention features a method that includes determining a pressure differential between the interior of the endoscope and the exterior of the endoscope while the endoscope is disposed in a treatment chamber, and regulating a pressure in the interior of the endoscope based on the pressure differential while the endoscope is disposed in the treatment chamber.

In one aspect, the invention features a computer program product residing on a computer readable medium having a plurality of instructions stored thereon which, when executed by one or more processors, cause the one or more processors to cause the occurrence of a process. The process includes transmitting light from a proximal end of an endoscope to a distal end of the endoscope through a longitudinal channel.

In another aspect, the invention features a computer program product residing on a computer readable medium having a plurality of instructions stored thereon which, when executed by one or more processors, cause the one or more processors to cause the occurrence of a process. The process includes sterilizing at least a portion of an interior of an endoscope while maintaining a pressure differential between the interior of the endoscope and an exterior of the endoscope of at most about five psi.

In a further aspect, the invention features a computer program product residing on a computer readable medium having a plurality of instructions stored thereon which, when executed by one or more processors, cause the one or more processors to cause the occurrence of a process. The process includes determining a pressure differential between the interior of an endoscope and the exterior of the endoscope while the endoscope is disposed in a treatment chamber, and regulating a pressure in the interior of the endoscope based on the pressure differential while the endoscope is disposed in the treatment chamber.

In certain embodiments, the methods allow data (e.g., data corresponding to the current status, historical status, and/or historical use for one or more reusable instruments, such as an endoscope) to be efficiently and accurately maintained, updated and accessed. Such data can include, for example, the sterilization status of the reusable instrument (e.g., the reusable medical instrument), the payment status of a client account associated with the reusable medical instrument (e.g., fully paid, delinquent, etc.), the maintenance status of the reusable instrument (e.g., whether the instrument has been used more than a predetermined number of times since it last underwent a maintenance procedure), and the supply status of the reusable instrument (e.g., whether the instrument has been used more than a predetermined number of times since the user was last provided appropriate supplies for the instrument).

Efficient, accurate and practical methods of charging a client for use of a medical instrument (e.g., a reusable medical instrument, such as an endoscope) are provided. The methods can allow, for example, for the client to be charged on a pay-per-use basis, or a pay-per-batch basis (per predetermined number of uses). The client can pay before or after use of the reusable instrument. In some embodiments, the charge to the client can be based on a number of factors, such as, for example, the identity of the client (e.g., whether the client is a private individual, a member of a professional organization, a private insurance agency, a private health maintenance organization, or a government agency), the number of times the client has used the medical instrument, the total number of times the client has used the reusable instrument, the number of times the client has used the treatment chamber (e.g., sterilization chamber, disinfection chamber), the total number of times the client has used any reusable instrument (e.g., as tracked by the system), the total number of times the client has used any treatment chamber (e.g., as tracked by the system), the time of day that the client used the instrument, and the frequency (e.g., on a per year basis, on a per month basis, on a per week basis) that the client has used the instrument.

Endoscopes are provided that have an indicator that provides the identity of the endoscope (as unique from all endoscopes). The identity can be based, for example, on the serial number of the endoscope or the product number of the endoscope.

Sensing devices are provided that can read information (e.g., identity, sterilization status, procedure enablement status) for a reusable instrument (e.g., reusable medical instrument, such as an endoscope). The sensing devices can be included in a system (e.g., a treatment chamber, such as a sterilization chamber), or the devices can be, for example, hand held. This can reduce the complexity associated with maintaining and tracking reusable instruments (e.g., reusable medical instruments, such as endoscopes), as well as reduce the complexity associated with billing for their use.

Endoscopes are provided that are untethered (can be used without external light sources, power sources, communication cables, etc.). This can reduce the cost and/or complexity associated with using, assembling and/or maintaining an endoscope.

Endoscopes are provided that can wirelessly transmit information (e.g., video data, endoscope position data) for display, for example, on an external monitor. This can reduce the complexity associated with using an endoscope in a medical procedure.

Reusable instrument treatment chambers (e.g., sterilization chambers, disinfection chambers) are provided that can be used to clean a reusable instrument (e.g., reusable medical instrument, such as an endoscope) to remove detritus with reduced cost and/or complexity.

Reusable instruments (e.g., reusable medical instruments) are provided that can be coupled to a pressure regulator to reduce pressure differentials during treatment (e.g., sterilization) of the instruments. This can result in a longer useful lifetime for the instruments. This can also reduce the presence of moisture (e.g., steam, water droplets) in undesirable portions of the interior of the reusable medical instrument (e.g., on optics in the elongated portion of an endoscope).

Features, objects and advantages of the invention are in the description, drawings and claims.

DETAILED DESCRIPTION

Figure 1:
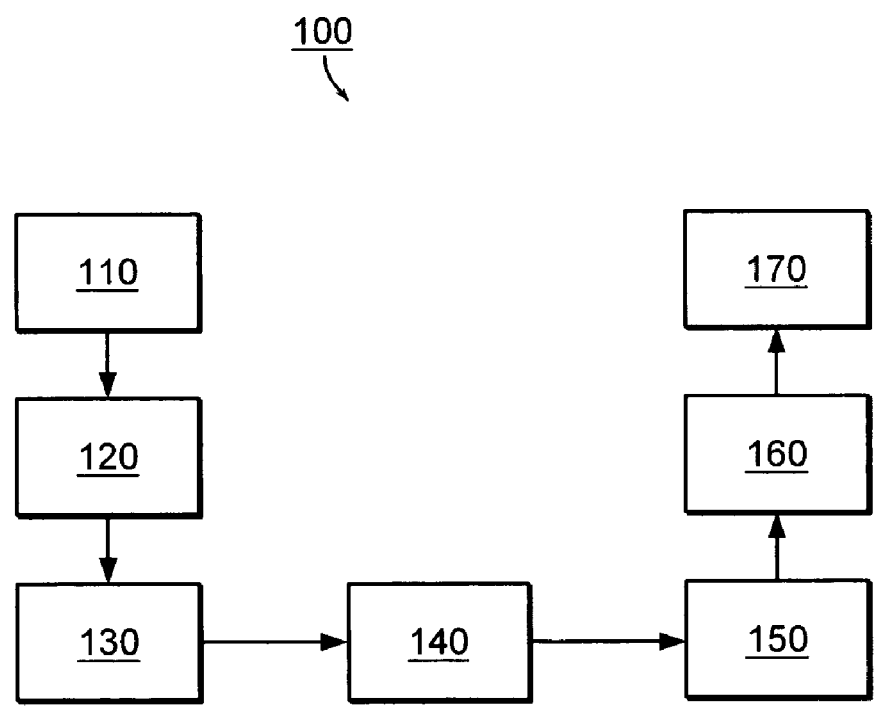
FIG. 1 is a flow chart of an embodiment of a method of using, cleaning, sterilizing and tracking an endoscope.

FIG. 1 is a flow chart of a method 100 of using an endoscope in a medical procedure, and subsequently cleaning and sterilizing the endoscope. First, the sterilization status (whether the endoscope has been sterilized since last used in a medical procedure) and the medical procedure enablement status (the status of one or more medical procedure enablement status factors, such as, for example, payment status, maintenance status, supply status) are determined (110). If the sterilization status and medical procedure enablement status are appropriate, the endoscope is used in a medical procedure (120), and the sterilization status and medical procedure enablement status of the endoscope are then updated (130). The endoscope is subsequently matched with an appropriate sterilization chamber (140), cleaned to at least partially remove detritus from the endoscope (150), and sterilized (160). Finally, the sterilization status and medical procedure enablement status of the endoscope are again updated (170).

Method 100 also allows certain information associated with the endoscope to be tracked during the process. As an example, the sterilization status of the endoscope can be tracked. This information can be used, for example, to reduce the risk of using the endoscope in multiple medical procedures without sterilizing the endoscope between uses. As another example, the medical procedure enablement status of the endoscope can be tracked. This information can be used, for example, to determine whether a client associated with the endoscope has been making appropriate payments for use of the endoscope (e.g., to disable the endoscope if the client account is delinquent), to reduce the risk of using the endoscope if it has not been properly maintained (e.g., to disable the endoscope if the endoscope has been used more than a predetermined number of times since it last underwent a maintenance procedure), and/or to reduce the risk that an operator will run out of supplies for the endoscope (e.g., to disable the endoscope if the endoscope has been used more than a predetermined number of times since the client was last provided supplies for the endoscope).

Endoscope Design

Figure 2:
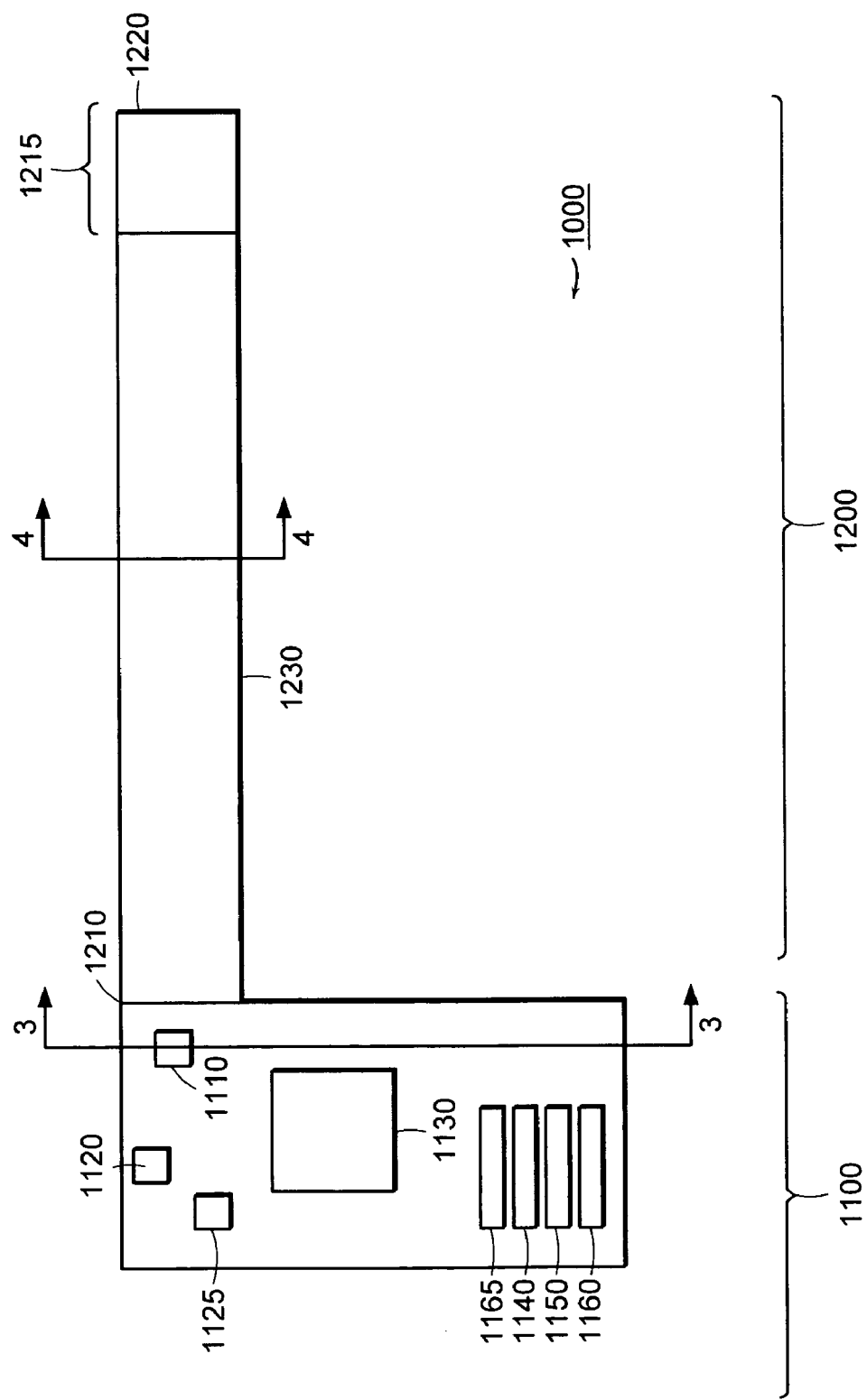
FIG. 2 is a side view of an embodiment of an endoscope.

FIG. 2 is a perspective view of an endoscope 1000 having a manipulation portion 1100 coupled to an elongated portion 1200. Manipulation portion 1100 is generally configured to remain outside a subject during use of endoscope 1000, and elongated portion 1200 is generally configured to be at least partially disposed within a subject during use of endoscope 1000. As explained below, endoscope 1000 is untethered (can be operated as an individual unit without being physically connected to external devices, such as light sources, power sources, communication cables or the like). Typically, endoscope 1000 is formed of one or more materials that can withstand sterilization conditions. Exemplary materials include Sil-Kore (W. L. Gore & Associates, Incorporated), Radel R-5000 (A. L. Hyde Company), stainless steel, autoclavable polytetrafluoroethylenes and autoclavable polypropylenes.

In general, endoscope 1000 is configured to be disposed within a body cavity (e.g., colon, stomach, esophagus, bronchi, larynx, urethra, kidneys, bladder, ear, nose) of a subject (e.g., a human, an animal) during use in a medical procedure. Examples of endoscopes include colonoscopes, gastroscopes, cystoscopes, laparoscopes, arthroscopes, and transesophageal ultrasonic instruments.

Figure 3:
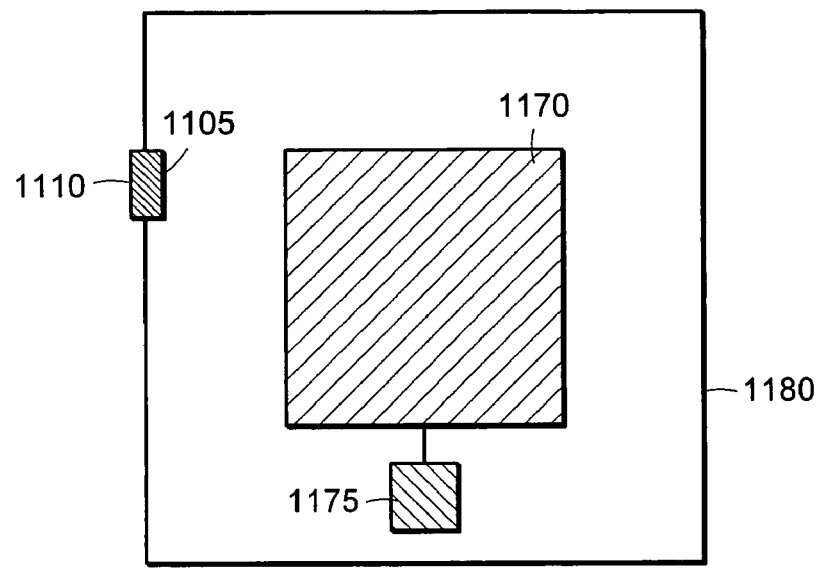
FIG. 3 is a cross-sectional view of the manipulation portion of the endoscope of FIG. 2.

As shown in FIGS. 2 and 3, manipulation portion 1100 includes an opening 1105, a seal 1110 in opening 1105, a control device 1120 (e.g., a switch, a hand wheel, a joystick), a control device 1130 (e.g., a switch, a valve, a hand wheel, a joystick). and a wireless transmitter 1125 (e.g., an IEEE 802.11 standard compatible wireless transmitter, a SIG Bluetooth standard compatible wireless transmitter), an image processor 1155 (shown in FIGS. 6 and 7) coupled to transmitter 1125, an identity indictor 1140, a sterilization status indicator 1150, a medical procedure enablement status indicator 1160, a sterilization chamber match indicator 1165, a light source 1170 (e.g., an incandescent light source, a florescent light source, a solid-state light source, an arc light source, a gas discharge light source) and corresponding power source 1175 (e.g., a battery, such as a rechargeable battery) housed inside wall 1180 of manipulation region 1100.

Figure 4:
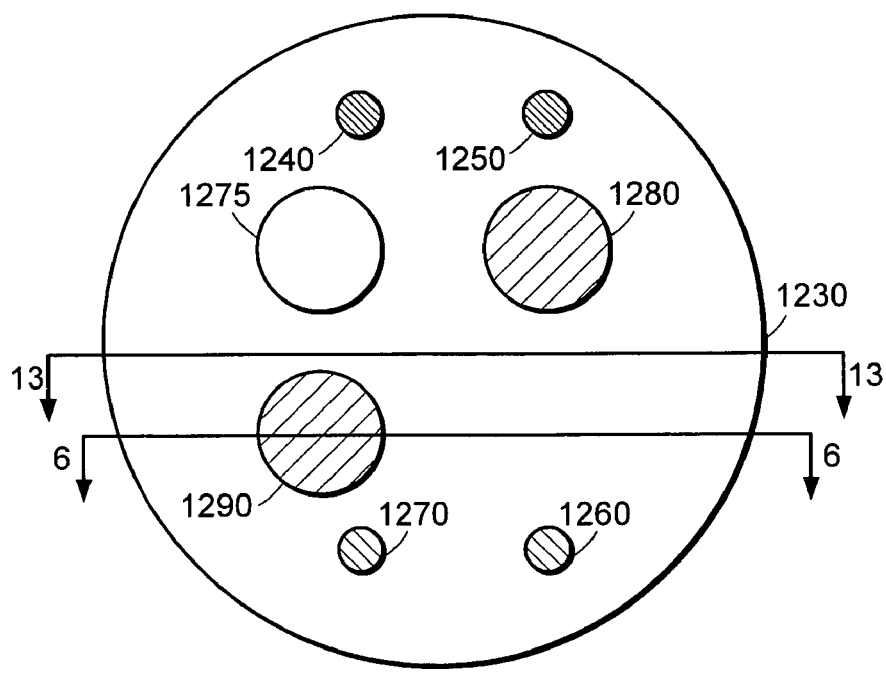
FIG. 4 is a cross-sectional view of the elongated portion of the endoscope of FIG. 2.

Referring to FIG. 2, elongated portion 1200 includes a proximal end 1210 coupled to manipulation portion 1100, a flexible portion 1215, and a distal end 1220. Referring to FIGS. 2 and 4 elongated portion 1200 has a wall 1230 that houses steering cables 1240, 1250, 1260 and 1270 that extend to distal end 1220, and are sealed at distal end 1220. Cables 1240, 1250, 1260 and 1270 are coupled (e.g., mechanically coupled, electrically coupled) to control devices 1120 and/or 1130 so that elongation portion 1200 can be positioned using the control device(s). Wall 1230 also houses an optical guide 1280 (e.g., a fiber optic conductor, a light transmissive cylinder, or a liquid-filled tube) that extends to distal end 1220, and is sealed at distal end 1220. Optical guide 1280 is optically coupled to light source 1270 (e.g., by contacting a flat surface of light source 1170 with a flat surface of optical guide 1280) so that light emitted by light source 1170 can travel along optical guide 1280 to distal end 1220. Wall 1230 further houses a working channel 1275 that extends to distal end 1220, and is open at distal end 1220. Working channel 1275 can be used, for example, to couple a medical tool at distal end 1220 with a control device on manipulation portion 1100, thereby allowing manipulation of the medical instrument using the control device. Wall 1230 also houses an optical image cable 1290 (e.g., a fiber optic conductor, wires conducting a video signal) adjacent distal end 1220, and is sealed at distal end 1220.

Use of Endoscope in a Medical Procedure

Generally, before using endoscope 1000 in a medical procedure, the sterilization status of endoscope 1000 (whether endoscope 1000 has been sterilized since last used in a medical procedure) and the medical procedure enablement status of endoscope 1000 (the status of one or more medical procedure enablement status factors, such as, for example, payment status, maintenance status, supply status) are determined. The sterilization status of endoscope 1000 can generally be determined by inspecting sterilization indicator 1150, and/or by using identity indicator 1140 (see discussion below). Similarly, the medical procedure enablement status of endoscope 1000 can generally be determined by inspecting medical procedure enablement status indicator 1160, and/or by using identity indicator 1140 (see discussion below). After verifying that both the sterilization status and the enablement status of endoscope 1000 are appropriate (e.g., endoscope 1000 has been sterilized since last used in a medical procedure, the account for the client associated with endoscope 1000 is not delinquent, endoscope 1000 has not been used more than a predetermined number of times since last undergoing a maintenance procedure, endoscope 1000 has not been used more than a predetermined number of times since the client was last provided supplies for endoscope 1000), endoscope 1000 can be used in a medical procedure.

Sterilization Status Indicator

In general, sterilization status indicator 1150 can be disposed in the interior of endoscope 1000 (e.g., in the interior of manipulation portion 1100, in the interior of elongated portion 1200), disposed on an exterior surface of endoscope 1000 (on an exterior surface of manipulation portion 1100, on the exterior surface of manipulation portion 1100), or integrally formed with endoscope 1000 (integrally formed with manipulation portion 1100, integrally formed with elongated portion 1200).

In some embodiments, sterilization status indicator 1150 can be visually inspected to determine the sterilization status of endoscope 1000. As an example, indicator 1150 can be formed of a material that changes color when exposed to sterilization conditions (e.g., from red to green), and again changes color (e.g., from green to red) when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids). As another example, indicator 1150 can be formed of a material that forms an image whose visibility changes (e.g., from nonvisible to visible, or from visible to nonvisible) when exposed to a sterilization cycle (e.g., so that a word, such as STERILIZED, appears on endoscope 1000 when exposed to sterilization, or so that a word, such as NONSTERILIZED, becomes nonvisible on endoscope 1000 when exposed to sterilization), and whose image reverts back to its prior state (visible to nonvisible, or nonvisible to visible) when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids). As a further example, indicator 1150 can be a marker (e.g., a colored marker) used in conjunction with a sleeve that moves to a certain position with respect to indicator 1150 when exposed to sterilization (e.g., sleeve moves to cover indicator 1150, or sleeve moves to expose indicator 1150), and that moves to a different position (e.g., sleeve moves to expose indicator 1150, or sleeve moves to cover indicator 1150) when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids).

In certain embodiments, sterilization status indicator 1150 contains information indicating the sterilization status of endoscope 1000 (e.g., sterilized since last used in a medical procedure, or not sterilized since last used in a medical procedure) that is designed to be read by a sensor (e.g., a hand held sensor) to determine the sterilization status of endoscope 1000 without knowing the identity of endoscope 1000. Such indicator/sensor systems include, for example, magnetic systems, inductance systems, electrical systems, optical systems, and/or mechanical systems. As an example, indicator 1150 and the sensor can be complimentary components of a mating key and socket mechanism. As another example, indicator 1150 and the sensor can be complimentary components of a passive electrical system (e.g., indicator 1150 is a passive electrical device, and the sensor is a sensor for such passive electrical devices). As a further example, indicator 1150 and the sensor can be complimentary components of a magnetic system (e.g., indicator 1150 is a magnetic binary code and the sensor has Hall effect sensors). As another example, indicator 1150 and the sensor can be complimentary components of a bar code system (e.g., indicator 1150 can be a bar code, and the sensor can be a bar code reader). As a further example, indicator 1150 and the sensor can be complimentary components to a dot code system (e.g., indicator 1150 can be a dot code, and the sensor can be a dot code reader). As a further example, indicator 1150 and the sensor can be complimentary components of an induction system (e.g., a passive induction system, such as a TIRIS system from Texas Instruments).

Alternatively or additionally, endoscope 1000 can be designed so that the sterilization status of endoscope 1000 can be determined by turning on power source 1175 and determining whether light is emitted by light source 1170 (e.g., by visually inspecting the distal end of optical guide 1280). As an example, endoscope 1000 can be designed so that, during sterilization, a thermal switch (e.g., a bimetallic switch) positions a flag outside the optical path between light source 1170 and optical guide 1280, and so that, when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids), the flag is positioned between light source 1170 and optical guide 1280 so that the flag blocks optical communication between light source 1170 and guide 1280. As another example, endoscope 1000 can be designed so that, during a sterilization cycle, a thermal switch (e.g., bimetallic spring) causes the focus to shift when the sterilization chamber begins to heat up, and resets the focus after the sterilization cycle. As an additional example, endoscope 1000 can be designed so that, during sterilization, an electrical connection between power source 1175 and light source 1170 is connected, and so that, when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids), the electrical connection between power source 1175 and light source 1170 is disconnected. As a further example, endoscope 1000 can be designed so that, during sterilization of endoscope 1000, power source 1175 is recharged (by removing power source 1175 from endoscope 1000 and charging power supply 1175 in a separate compartment while endoscope 1000 is being sterilized, or by charging power source 1175 during sterilization without removal from endoscope 1000), and so that when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids), power source 1175 is discharged.

Alternatively or additionally, endoscope 1000 can be designed so that the sterilization status of endoscope 1000 can be determined by turning on power source 1175 and determining whether light transmitted from distal end 1220 along optical image cable 1290 to manipulation portion 1100 (e.g., by determining whether processor 1155 receives a signal from cable 1290). As an example, endoscope 1000 can be designed so that, during sterilization, a thermal switch.(e.g., a bimetallic switch) positions a flag outside the optical path between the distal end of cable 1290 and processor 1155, and so that, when more than a predetermined period of time lapses after sterilization (e.g., more than about one day, more than about one week) or when endoscope 1000 is exposed to conditions similar to those experienced during a medical procedure (e.g., when endoscope 1000 is held at a temperature of about 37° C., when endoscope 1000 is exposed to body fluids), the flag is positioned between the distal end of cable 1290 and processor 1155 so that the flag blocks optical communication between the distal end of cable 190 and processor 1155.

Alternatively or additionally, endoscope 1000 can be designed so that the sterilization status of endoscope 1000 can be determined by determining whether an articulation mechanism of endoscope 1000 works. For example, endoscope 1000 can be designed so that, during a sterilization cycle, a thermal switch (e.g., bimetallic spring) applies a brake to an articulation mechanism when the autoclave heats up, and the sterilization system releases the brake upon completion of the sterilization cycle.

Medical Procedure Enablement Status Indicator

In general, medical procedure enablement status indicator 1160 can be disposed in the interior of endoscope 1000 (e.g., in the interior of manipulation portion 1100, in the interior of elongated portion 1200), disposed on an exterior surface of endoscope 1000 (on an exterior surface of manipulation portion 1100, on the exterior surface of manipulation portion 1100), or integrally formed with endoscope 1000 (integrally formed with manipulation portion 1100, integrally formed with elongated portion 1200).

In some embodiments, medical procedure enablement status indicator 1160 can be visually inspected to determine the medical procedure enablement status of endoscope 1000. As an example, indicator 1160 can be formed of a material that has one color if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), and a different color if the factor has a different status (account delinquent, more than a predetermined number of uses of endoscope 1000 since its last maintenance procedure, more than a predetermined number of uses of endoscope 1000 since supply materials were acquired). As another example, indicator 1160 can be formed of a material that forms an image that has one visibility status (e.g., nonvisible, visible) if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), and a different visibility status (e.g., visible or nonvisible) if the factor has a different status (account delinquent, more than a predetermined number of uses of endoscope 1000 since its last maintenance procedure, more than a predetermined number of uses of endoscope 1000 since supply materials were acquired). As a further example, indicator 1160 can be a marker (e.g., a colored marker) used in conjunction with a sleeve that moves to a certain position with respect to indicator 1160 (e.g., sleeve moves to cover indicator 1160, or sleeve moves to expose indicator 1160) if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), and that moves to a different position (e.g., sleeve moves to expose indicator 1160, or sleeve moves to cover indicator 1160) if the factor has a different status (account delinquent, more than a predetermined number of uses of endoscope 1000 since its last maintenance procedure, more than a predetermined number of uses of endoscope 1000 since supply materials were acquired).

In certain embodiments, medical procedure enablement status indicator 1160 contains information regarding the medical procedure enablement status of endoscope 1000 (e.g., account payment status, endoscope 1000 maintenance status, endoscope 1000 supply status) that is designed to be read by a sensor (e.g., a hand held sensor) to determine the medical procedure enablement status of endoscope 1000 without knowing the identity of endoscope 1000. Such indicator/sensor systems include, for example, magnetic systems, inductance systems, electrical systems, optical systems, and/or mechanical systems. As an example, indicator 1160 and the sensor can be complimentary components of a mating key and socket mechanism. As another example, indicator 1160 and the sensor can be complimentary components of a passive electrical system (e.g., indicator 1160 is a passive electrical device, and the sensor is a sensor for such passive electrical devices). As a further example, indicator 1160 and the sensor can be complimentary components of a magnetic system (e.g., indicator 1160 is a magnetic binary code and the sensor has Hall effect sensors). As another example, indicator 1160 and the sensor can be complimentary components of a bar code system (e.g., indicator 1160 can be a bar code, and the sensor can be a bar code reader). As a further example, indicator 1160 and the sensor can be complimentary components to a dot code system (e.g., indicator 1160 can be a dot code, and the sensor can be a dot code reader). As a further example, indicator 1160 and the sensor can be complimentary components of an induction system (e.g., a passive induction system, such as a TIRIS system from Texas Instruments).

Alternatively or additionally, endoscope 1000 can be designed so that the medical procedure enablement status of endoscope 1000 can be determined by turning on power source 1175 and determining whether light is emitted by light source 1170 (e.g., by visually inspecting the distal end of optical guide 1280). As an example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), a flag is positioned outside the optical path between light source 1170 and optical guide 1280, and so that, if the factor has a different status (account delinquent, more than a predetermined number of uses of endoscope 1000 since its last maintenance procedure, more than a predetermined number of uses of endoscope 1000 since supply materials were acquired), the flag is positioned between light source 1170 and optical guide 1280 so that the flag blocks optical communication between light source 1170 and guide 1280. As another example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), the optics in endoscope 1000 are properly focused, and so that, if the factor has a different status (account delinquent, more than a predetermined number of uses of endoscope 1000 since its last maintenance procedure, more than a predetermined number of uses of endoscope 1000 since supply materials were acquired), the optics are not properly focused. As an additional example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), an electrical connection between power source 1175 and light source 1170 is connected, and so that, if the factor has a different status (account delinquent, more than a predetermined number of uses of endoscope 1000 since its last maintenance procedure, more than a predetermined number of uses of endoscope 1000 since supply materials were acquired), the connection is disconnected. As a further example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), power source 1175 is charged, and so that, if the factor has a different status (account delinquent, more than a predetermined number of uses of endoscope 1000 since its last maintenance procedure, more than a predetermined number of uses of endoscope 1000 since supply materials were acquired), power source 1175 is discharged.

Alternatively or additionally, endoscope 1000 can be designed so that the medical procedure enablement status of endoscope 1000 can be determined by turning on power source 1175 and determining whether light transmitted from distal end 1220 along optical image cable 1290 to manipulation portion 1100 (e.g., by determining whether processor 1155 receives a signal from cable 1290). As an example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), a flag is positioned outside the optical path between the distal end of cable 1290 and processor 1155, and so that if the medical procedure enablement status factor associated with endoscope 1000 has a different status (e.g., account delinquent, more than a predetermined number of uses of endoscope 1000 since its last maintenance procedure, more than a predetermined number of uses of endoscope 1000 since supply materials were acquired), the flag is positioned between the distal end of cable 1290 and processor 1155 so that the flag blocks optical communication between the distal end of cable 190 and processor 1155.

Alternatively or additionally, endoscope 1000 can be designed so that the medical procedure enablement status of endoscope 1000 can be determined by determining whether an articulation mechanism of endoscope 1000 works. For example, endoscope 1000 can be designed so that, if a given medical procedure enablement status factor associated with endoscope 1000 has a particular status (e.g., fully paid, less than a predetermined number of uses of endoscope 1000 since its last maintenance procedure, less than a predetermined number of uses of endoscope 1000 since supply materials were acquired), an articulation element functions properly, and so that, if the factor has a different status (e.g., account delinquent, more than a predetermined number of uses of endoscope 1000 since its last maintenance procedure, more than a predetermined number of uses of endoscope 1000 since supply materials were acquired), the articulation element is prevented from functioning properly (e.g., by applying a brake to the articulation mechanism).

Identity Indicator

Figure 5:
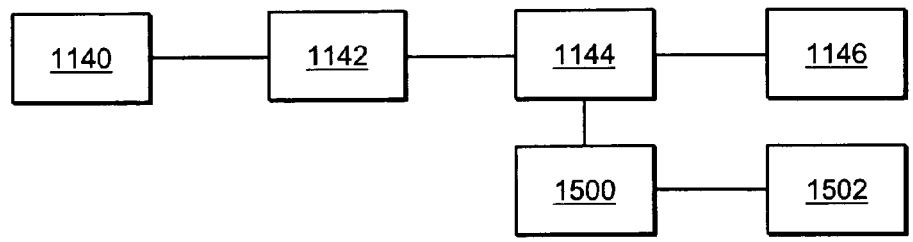
FIG. 5 is a schematic diagram of an embodiment of a system for reading an identity indicator.

In some embodiments, the sterilization status and/or medical procedure enablement status of endoscope 1000 is determined by reading identity indicator 1140 (e.g., without reading sterilization status indicator 1150 and/or medical procedure enablement status indicator 1160). Referring to FIG. 5, an identity sensor 1142 reads data from identity indicator 1140 (data corresponding to the identity of endoscope 1000), and passes the data to data processor 1144 (e.g., a computer). Based on the data from indicator 1140, data processor 1144 accesses appropriate data (e.g., sterilization status data, medical procedure enablement status data) for endoscope 1000 contained in a database stored on a data storage device 1146 (e.g., a hard disk drive, a random access memory, a read-only memory).

In certain embodiments, data processor 1144 may be in communication with one or more status adjustment devices (e.g., a sterilization status adjustment device, a medical procedure enablement status adjustment device) so that processor 1144 can instruct the device to change the status of one or more indicators for endoscope 1000 (e.g., to change the status of sterilization status indicator 1150, to change the status of medical procedure enablement device status indicator 1160) based on the information that processor 1144 receives from device 1146. Processor 1144 can also send appropriate data to device 1146 to update data contained in the database contained on device 1146 for endoscope 1000 (e.g., to update data in the database for endoscope 1000 to indicate that the sterilization status for endoscope 1000 has changed, to update data in the database for endoscope 1000 to indicate that the medical procedure enablement status for endoscope 1000 has changed). For example, referring to FIG. 5, processor 1144 is in communication with a status adjustment device 1500 (e.g., a sterilization indicator status adjustment device, a medical procedure enablement status adjustment device) that is configured to change the status of an indicator 1502 (e.g., a sterilization status indicator, a medical procedure enablement status indicator) for endoscope 1000, and processor 1144 is also in communication with device 1146 to appropriately update data in the database for endoscope 1000.

In some embodiments, status adjustment device 1500 forms a complimentary component of indicator 1502 (e.g., a magnetic device, an inductance device, an electrical device, an optical device, a mechanical device). As an example, device 1500 and indicator 1502 can be complimentary components of a mating key and socket mechanism so that device 1500 can change the position of indicator 1502, thereby changing the status of endoscope 1000 as indicated by indicator 1502. As another example, device 1500 and indicator 1502 can be complimentary components of a passive electrical system so that device 1500 can change a passive electrical property of indicator 1502, thereby changing the status of endoscope 1000 as indicated by indicator 1502. As a further example, device 1500 and indicator 1502 can be complimentary components of a magnetic system so that device 1500 can change a magnetic property of indicator 1502, thereby changing the status of endoscope 1000 as indicated by indicator 1502. As another example, device 1500 and indicator 1502 can be complimentary components of a bar code system so that device 1500 can change the bar code of indicator 1502, thereby changing the status of endoscope 1000 as indicated by indicator 1502. As a further example, device 1500 and indicator 1502 can be complimentary components of a dot code system so that device 1500 can change the dot code of indicator 1502, thereby changing the status of endoscope 1000 as indicated by indicator 1502. As another example, device 1500 and indicator 1502 can be complimentary components of an induction system so that device 1500 can change the passive induction properties of indicator 1502, thereby changing the status of endoscope 1000 as indicated by indicator 1502. As an additional example, device 1500 can be capable of heating endoscope 1500 to affect a color change in indicator 1502, thereby changing the status of endoscope 1000 as indicated by indicator 1500. As a further example, indicator 1502 can be capable of heating endoscope 1000 to affect a change in the visibility (e.g., visible to nonvisible, nonvisible to visible) of indicator 1502, thereby changing the status of endoscope 1000 as indicated by indicator 1502. As another example, indicator 1502 can be capable of changing the position of a sleeve relative to indicator 1502 (e.g., indicator 1502 covered by sleeve to indicator 1502 not covered by sleeve, indicator 1502 not covered by sleeve to indicator 1502 covered by sleeve) on endoscope 1000, thereby changing the status of endoscope 1000 as indicated by indicator 1502.

In certain embodiments, status adjustment device 1500 can adjust the status of endoscope 1000 (e.g., sterilization status, medical procedure enablement status) without interacting with indicator 1502 (e.g., sterilization status indicator, medical procedure enablement status indicator). As an example, device 1500 can be capable of changing (e.g., by thermally activating a bimetallic spring) the position of a flag so that the flag is positioned in/outside the optical path between light source 1170 (e.g., see FIG. 3) and the distal end of optical guide 1280. As another example, device 1500 can be capable of changing (e.g., by thermally activating a bimetallic spring) the focus of the optics in endoscope 1000. As an additional example, device 1500 can be capable of connecting/disconnecting (e.g., by thermally activating a bimetallic switch) an electrical connection between power source 1175 and light source 1170, or between a power source and a video camera. As a further example, device 1500 can be capable of charging/discharging power source. As another example, device 1500 can be capable of applying/removing a brake on an articulation mechanism of endoscope 1000.

Performing a Medical Procedure

After verifying that both the sterilization status and medical procedure enablement status of endoscope 1000 are appropriate, endoscope 1000 can be used by an operator (e.g., a surgeon) in a medical procedure as follows.

Figure 6:
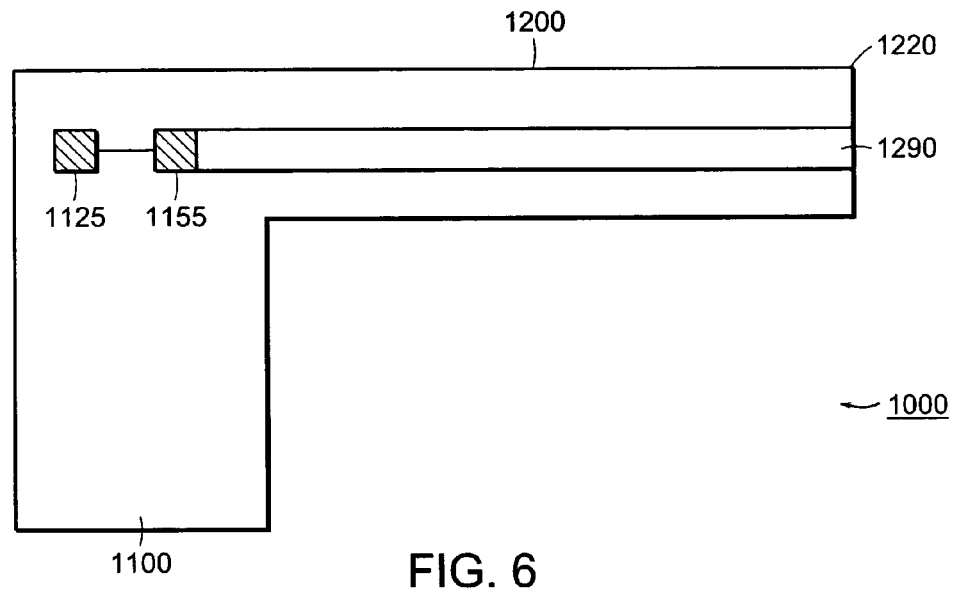
FIG. 6 is a partial cross-sectional view of the elongated portion of the endoscope of FIG. 2.
Figure 7:
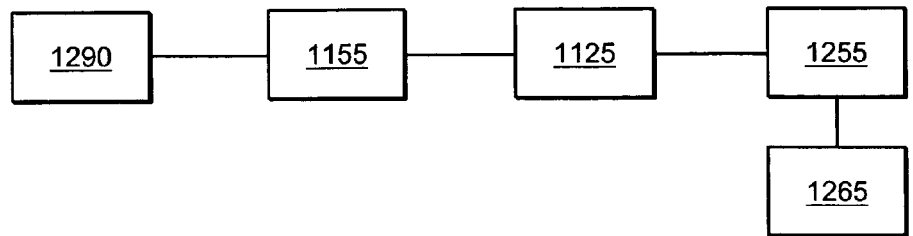
FIG. 7 is a schematic diagram of an embodiment of a system for wirelessly transmitting data from the endoscope of FIG. 2.

The operator turns on power source 1175 (e.g., using a control device on manipulation portion 1100) so that light travels from light source 1170 and along optical guide 1280 to distal end 1220 where the light illuminates a region inside the subject that is adjacent distal end 1220. Referring to FIGS. 6 and 7, optical image cable 1290 is coupled to an image processor 1155, which, in turn, is coupled to wireless transmitter 1125 so that visual data received by cable 1290 is wirelessly transmitted by transmitter 1125. Transmitter 1125 is coupled to a data processor 1255 (e.g., via a wireless receiver), which, in turn, is coupled to a display device 1265 (e.g., a video monitor) so that the data transmitted by transmitter 1125 is displayed on display device 1265. The operator of endoscope 1000 analyzes the displayed information, and uses control devices 1120 and/or 1130 to manipulate flexible portion 1215 via steering guides 1240, 1250, 1260 and/or 1270 to adjust the position of elongated portion 1200 within the subject. Alternatively or additionally, wireless transmitter 1125 can be used in conjunction with a receiver (e.g., an RF receiver) to provide data corresponding to the position of distal end 1220 within the subject, and the wirelessly received signal can be used, for example, to position endoscope 1000 within the subject. Alternatively or additionally, endoscope 1000 can include a receiver configured to receive a wireless transmission (e.g., from a wireless transmitter outside the subject). Optionally, a medical tool (e.g., a cauterizing apparatus, a cutting apparatus, a clamping apparatus, an irrigation apparatus, a suction apparatus, a pressurization apparatus, an inspection apparatus, a marking apparatus, an illumination apparatus, a retrieval apparatus) can be positioned at distal end 1220 and coupled to a control device on manipulation portion 1100 through working channel 1275 (see FIG. 4) so that the medical instrument can be manipulated (e.g., based on the visual information and/or position information) using a control device (e.g., positioned on manipulation portion 1100).

Updating Endoscope Status

After using endoscope 1000 in a medical procedure, the sterilization status and/or medical procedure enablement status of endoscope 1000 can be updated.

In some embodiments, using endoscope 1000 in a medical procedure automatically updates sterilization status of endoscope 1000 (e.g., as indicated by sterilization status indicator 1150) to indicate that endoscope 1000 has not been sterilized since last used in a medical procedure. As an example, indicator 1150 may change color (e.g., green to red) to indicate that endoscope 1000 has not been sterilized since last used in a medical procedure. As another example, indicator 1150 may display a word (e.g., NONSTERILIZED) to indicate that endoscope 1000 has not been sterilized since last used in a medical procedure. As a further example, indicator 1150 may cover/not cover a marker on endoscope 1000 to indicate that endoscope 1000 has not been sterilized since last used in a medical procedure. In some embodiments, the distal end of optical guide 1280 may not emit light when power source 1175 is turned on to indicate that endoscope 1000 has not been sterilized since last used in a medical procedure. In certain embodiments, an articulation element may fail to function properly to indicate that endoscope 1000 has not been sterilized since last used in a medical procedure.

In certain embodiments, using the endoscope in a medical procedure automatically updates the medical procedure enablement status of endoscope 1000 (e.g., as indicated by indicator 1160) to indicate that endoscope 1000 should not be used in a medical procedure and/or to prevent endoscope 1000 from being used in a medical procedure (e.g., by disabling endoscope 1000 from being capable of being used in a medical procedure). As an example, indicator 1160 may change color (e.g., green to red) to indicate that endoscope 1000 should not be used in a medical procedure. As another example, indicator 1160 may display a word (e.g., DISABLED) to indicate that endoscope 1000 should not be used in a medical procedure. As a further example, indicator 1150 may cover/not cover a marker on endoscope 1000 to indicate that endoscope 1000 should not be used in a medical procedure. In some embodiments, the distal end of optical guide 1280 may not emit light when power source 1175 is turned on to indicate that endoscope 1000 has been disabled from being used in a medical procedure. In certain embodiments, an articulation element may fail to function properly to indicate that endoscope 1000 has been disabled from being used in a medical procedure.

In some embodiments, the sterilization status and/or medical procedure enablement status of endoscope 1000 is updated using identity indicator 1140 (e.g., without updating sterilization status indicator 1150 and/or medical procedure enablement status indicator 1160). For example, again referring to FIG. 5, identity sensor 1142 reads data from identity indicator 1140 (data corresponding to the identity of endoscope 1000), and passes the data to data processor 1144. Processor 1144 sends appropriate data to device 1146 to update data contained in the database contained on device 1146 for endoscope 1000 (e.g., to update data in the database for endoscope 1000 to indicate that endo scope 1000 has not been sterilized since last used in a medical procedure). Processor 1144 may instruct status adjustment device 1500 to update the status of an indicator (e.g., a sterilization status indicator) using an appropriate status adjustment device (see discussion above). In some embodiments, processor 1144 may read certain data for endoscope 1000 in the database for endoscope 1000 on device 1146 (e.g., medical procedure enablement status data), and update the status of the corresponding indicator (e.g., medical procedure enablement status indicator) for endoscope 1000 (see discussion above).

Cleaning and Sterilization of Endoscope

In general, after use in a medical procedure, endoscope 1000 is cleaned to remove detritus, and then sterilized.

Sterilization Chamber

Figure 8:
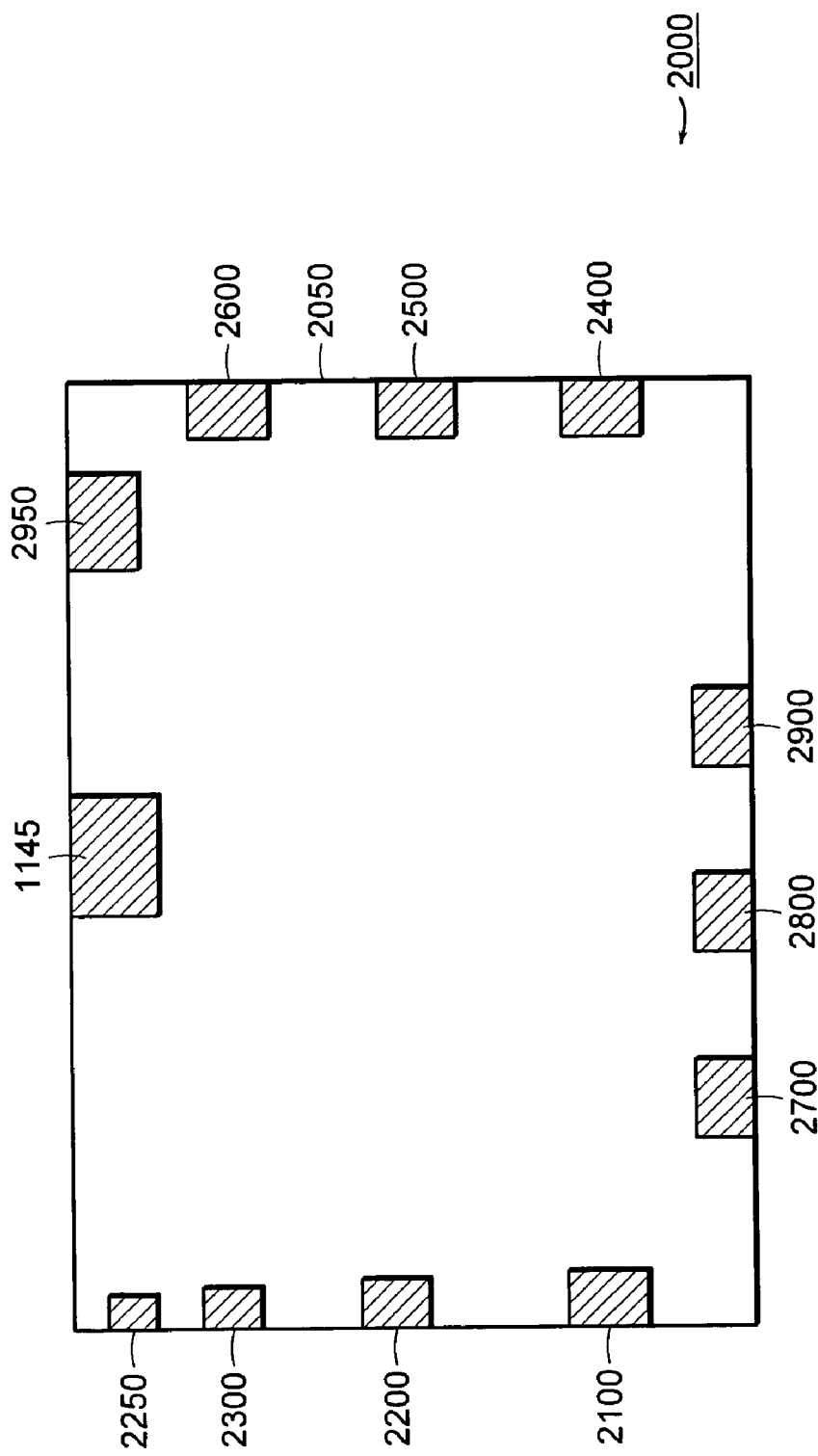
FIG. 8 is a cross-sectional view of an embodiment of a sterilization chamber.

FIG. 8 is a cross-sectional view of a sterilization chamber 2000 configured to clean and sterilize endoscope 1000. Sterilization chamber 2000 has a wall 2050 that houses an identity sensor 2100, a sterilization status adjustment device 2200, a medical procedure enablement status adjustment device 2300, a sterilization match sensor 2250, a cleaning device 2400 designed to clean the interior of working channel 1275, a cleaning device 2500 designed to clean the exterior surface of wall 1230, a fluid emission device 2600 designed to emit a fluid into working channel 1275, a pressure regulator 1145, a pressure sensor 2700, a temperature sensor 2800, a timer 2900, and a communication device 2950 (e.g., a wireless transmitter, a transmitter electrically connected to processor 1144, a transmitter optically connected to processor 1144, a wireless receiver, a receiver electrically connected to processor 1144, a receiver optically connected to processor 1144, a wireless transmitter/receiver, a transmitter/receiver electrically connected to processor 1144, a transmitter/receiver optically connected to processor 1144). Each of sensor 2100, device 2200, device 2300, sensor 2250, device 2300, device 2400, device 2500, sensor 2700, sensor 2800, sensor 2900, and/or device 2950 can be integral with chamber 2000, disposed in the interior of chamber 2000, or disposed on the exterior of chamber 2000.

Matching Endoscope and Sterilization Chamber

Sterilization chamber 2000 is designed to ensure that endoscope 1000 is properly matched with chamber 2000 (e.g., to avoid damage to endoscope 1000 due to exposure to improper sterilization conditions, to avoid ineffective sterilization of endoscope 1000 due to improper sterilization conditions, to be able to monitor use of endoscope 1000). Sterilization chamber 2000 is also designed to be capable of interacting with the database for endoscope 1000 stored on device 1146 (e.g., to determine status information for endoscope 1000, to update status information for endoscope 1000, to determine status information for chamber 2000, to update status information for chamber 2000).

In general, sterilization chamber match indicator 1165 can be disposed in the interior of endoscope 1000 (e.g., in the interior of manipulation portion 1100, in the interior of elongated portion 1200), disposed on an exterior surface of endoscope 1000 (on an exterior surface of manipulation portion 1100, on the exterior surface of manipulation portion 1100), or integrally formed with endoscope 1000 (integrally formed with manipulation portion 1100, integrally formed with elongated portion 1200).

In certain embodiments, sterilization chamber match indicator 1165 contains information that can be read by sterilization chamber match sensor 2250 to determine if endoscope 1000 matches sterilization chamber 2000 without knowing the identity of endoscope 1000. Such indicator/sensor systems include, for example, magnetic systems, inductance systems, electrical systems, optical systems, and/or mechanical systems. As an example, indicator 1165 and sensor 2250 can be complimentary components of a mating key and socket mechanism. As another example, indicator 1165 and sensor 2250 can be complimentary components of a pressure interlock mechanism. As another example, indicator 1165 and sensor 2250 can be complimentary components of a passive electrical system (e.g., indicator 1165 is a passive electrical device, and sensor 2250 is a sensor for such passive electrical devices). As a further example, indicator 1165 and sensor 2250 can be complimentary components of a magnetic system (e.g., indicator 1165 is a magnetic binary code and sensor 2250 has Hall effect sensors). As another example, indicator 1165 and sensor 2250 can be complimentary components of a bar code system (e.g., indicator 1165 can be a bar code, and sensor 2250 can be a bar code reader). As a further example, indicator 1165 and sensor 2250 can be complimentary components to a dot code system (e.g., indicator 1165 can be a dot code, and sensor 2250 can be a dot code reader). As a further example, indicator 1165 and sensor 2250 can be complimentary components of an induction system (e.g., a passive induction system, such as a TIRIS system from Texas Instruments).

Figure 9:
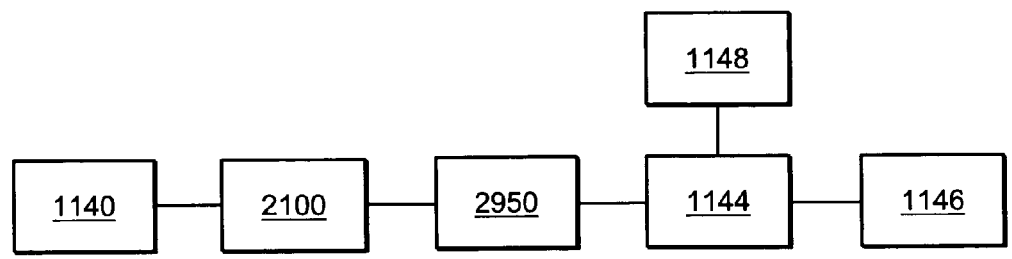
FIG. 9 is a schematic diagram of an embodiment of a system for reading an identity indicator.

In some embodiments, the match between endoscope 1000 and sterilization chamber 2000 can be determined using identity indicator 1140 (e.g., without using indicator 1165. Referring to Fig. 9, identity sensor 2100 reads data from identity indicator 1140 (data corresponding to the identity of endoscope 1000), and passes the data to data processor 1144 via device 2950. Processor 1144 retrieves appropriate data to device 1146 to detennine whether endoscope 1000 matches sterilization chamber 2000. If endoscope 1000 does not match sterilization chamber 2000, then processor 1144 instructs a power supply 1148 to shut down sterilization chamber 2000.

Cleaning Endoscope to Remove Detritus

After determining that endoscope 1000 matches sterilization chamber 2000, chamber 2000 cleans endoscope 1000 to remove detritus.

Figure 10:
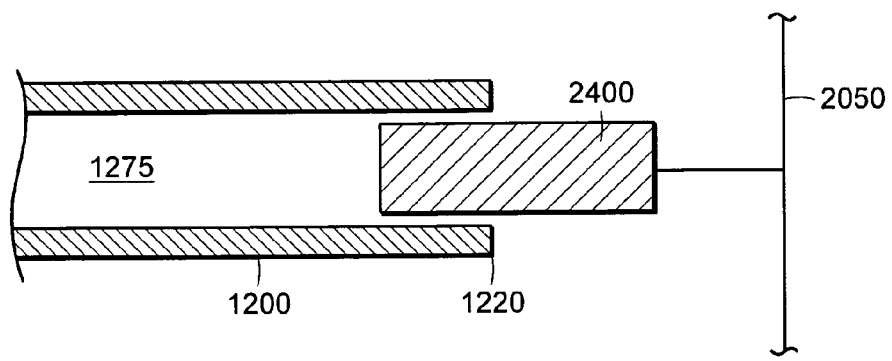
FIG. 10 is a partial cross-section view of the sterilization chamber of FIG. 8 and a portion of the endoscope of FIG. 2.
Figure 11:
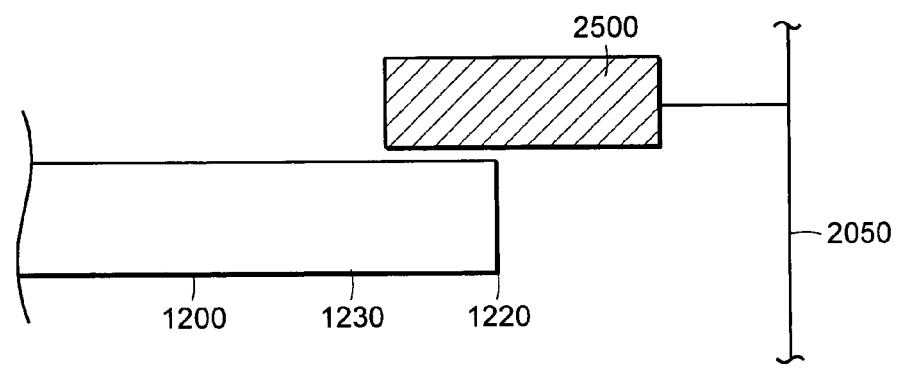
FIG. 11 is a partial cross-sectional view of the sterilization chamber of FIG. 8 and a portion of the endoscope of FIG. 2.
Figure 12:
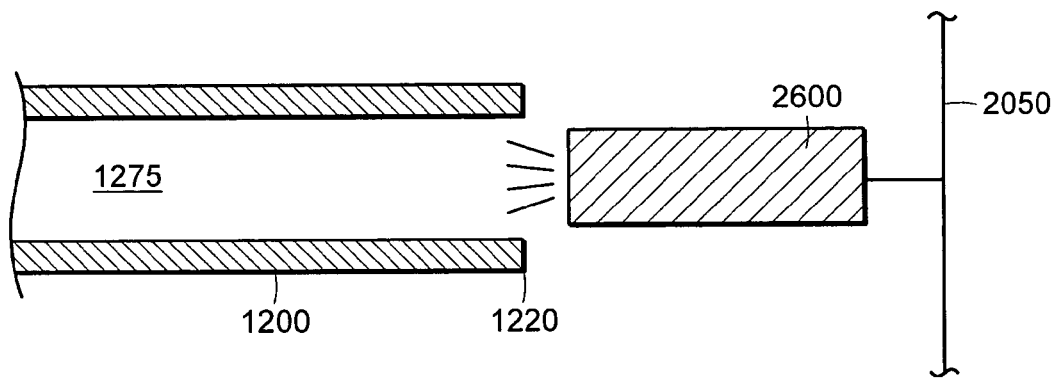
FIG. 12 is a partial cross-sectional view of the sterilization chamber of FIG. 8 and a portion of the endoscope of FIG. 2.

Referring to FIGS. 10 and 12, for clarity purposes, only a portion of endoscope 1000 is shown. Specifically, working channel 1275 within elongated portion 1200 is shown in isolation in the partial cross-sectional view of FIGS. 10–12. That is, steering cables 1240, 1250, 1260, 1270, optical guide 1280, and optical image cable 1290, which are all housed within wall 1230 and sealed at distal end 1220, as shown in FIG. 4, are not shown in FIGS. 10 and 12 for clarity purposes.

Referring to FIG. 10, cleaning device 2400 (e.g., a brush, a fluid emission device, a radiation emission device, a pipe cleaner, a thread, a rope) is disposed within working channel 1275, and relative motion occurs between working channel 1275 and cleaning device 2400 so that cleaning device 2400 interacts with different regions of working channel 1275 to clean working channel 1275 (e.g., to brush off detritus, to blow off detritus with fluid). In general, the manner in which cleaning device 2400 is disposed in working channel 1275, and relative motion occurs can be varied as desired. In some embodiments, cleaning device 2400 is stationary and configured so that, as endoscope 1000 (see FIGS. 2 and 4) is disposed in sterilization chamber 2000, device 2400 is placed within channel 1275. In certain embodiments, cleaning device 2400 is movable within sterilization chamber 2000 so that, after endoscope 1000 is disposed in sterilization chamber 2000, device 2400 is moved into working channel 1275. In some embodiments, after at least partially disposing device 2400 within channel 1275, cleaning device 2400 moves within channel 1275 while channel 1275 is stationary. In certain embodiments, after at least partially disposing device 2400 within channel 1275, working channel 1275 moves while device 2400 is stationary. Generally, the movement of cleaning device 2400 andlor channel 1275 can be manual controlled, automated or both.

Referring to FIG. 11, before, after or while cleaning device 2400 cleans channel 1275, cleaning device 2500 (e.g., a brush, a fluid emission device, a radiation emission device, a pipe cleaner, a thread, a rope) and the exterior surface of wall 1230 are positioned adjacent each other, and relative motion occurs between cleaning device 2500 and wall 1230 so that cleaning device 2500 interacts with different regions of the exterior of wall 1230 to clean wall 1230 (e.g., to brush off detritus, to blow off detritus with fluid). In general, the manner in which cleaning device 2500 and wall 1230 are disposed adjacent each other and relative motion occurs can be varied as desired. In some embodiments, cleaning device 2500 is stationary and configured so that, as endoscope 1000 is disposed in sterilization chamber 2000, device 2500 is placed adjacent the exterior of wall 1230. In certain embodiments, cleaning device 2500 is movable within sterilization chamber 2000 so that, after endoscope 1000 is disposed in sterilization chamber 2000, device 2500 is moved adjacent the exterior of wall 1230. In some embodiments, after disposing the exterior of wall 1230 and device 2500 adjacent each other, cleaning device 2500 moves adjacent different regions of the exterior of wall 1230 while wall 1230 is stationary. In certain embodiments, after disposing the exterior of wall 1230 and device 2500 adjacent each other, wall 1230 moves while device 2500 is stationary. In general, the movement of cleaning device 2500 andlor wall 1230 can be manually controlled, automated or both.

Referring to FIG. 12, alternatively or additionally, fluid emission device 2600 (e.g., a steam emission nozzle, a steam emission hose, a gas emission nozzle, a gas emission hose, a cleaning fluid emission nozzle, a cleaning emission hose) can be positioned adjacent working channel 1275 at distal end 1220, and device 2600 can emit a fluid into channel 1275 to clean channel 1275. In general, the manner in which cleaning device 2600 and channel 1275 are disposed adjacent each other can be varied as desired. In some embodiments, cleaning device 2600 is stationary and configured so that, as endoscope 1000 is disposed in sterilization chamber 2000, device 2600 is placed adjacent channel 1275 at distal end 1220. In certain embodiments, cleaning device 2600 is movable within sterilization chamber 2000 so that, after endoscope 1000 is disposed in sterilization chamber 2000, device 2600 is moved adjacent channel 1275 at distal end 1220. In general, the movement of cleaning device 2600 and/or channel 1275 can be manually controlled, automated or both. Cleaning device 2600 can emit, for example, one or more enzymatic cleaning fluids, disinfectant fluids, and/or sterilization fluids.

Sterilization of Endoscope

After cleaning endoscope 1000 to remove detritus, endoscope 1000 is sterilized. Generally, sterilization includes sealing sterilization chamber 2000, evacuating chamber 2000, and introducing pressurized steam into chamber 2000. The steam pressure, steam temperature, and the amount of time to which the endoscope is exposed to the steam can be selected on the particular type of endoscope (e.g., materials, size, uses).

In general, sterilization of endoscope 1000 involves first evacuating chamber 2000, and then pressurizing chamber 2000 with steam. Elongated portion 1200 of endoscope 1000 typically has one or more components that are sealed at distal end 1220 (e.g., steering cables, an optical guide, an optical image cable), which can cause pressure differentials to occur during the sterilization process. For example, during evacuation of chamber 2000, endoscope 1000 can partially expand due to a pressure differential between the exterior of endoscope 1000 (relatively low pressure) and the region of endoscope 1000 that is sealed at distal end 1220 (relatively high pressure), and, during pressurization of chamber 2000, endoscope 1000 can partially collapse due to a pressure differential between the exterior of endoscope 1000 (relatively high pressure) and the region of endoscope 1000 that is sealed at distal end 1220 (relatively low pressure).

Figure 13:
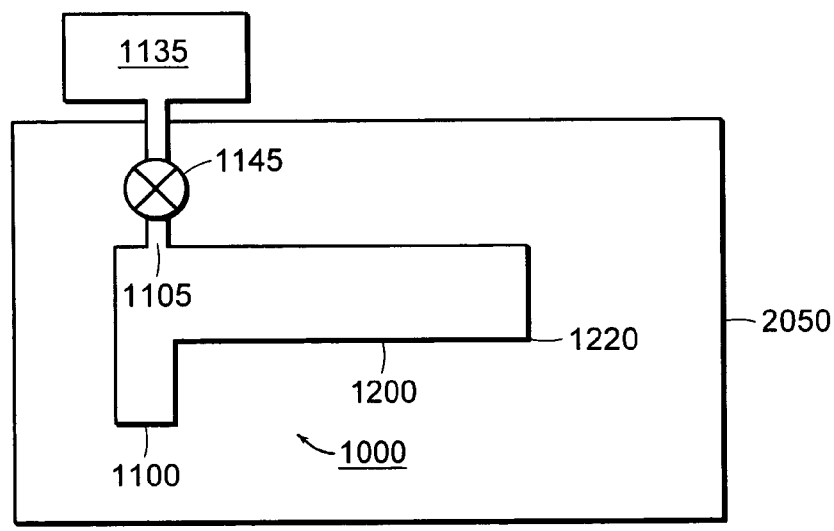
FIG. 13 is a partial cross-sectional view of the sterilization chamber of FIG. 8 containing the endoscope of FIG. 2.

FIG. 13 shows a cross-section of a portion of endoscope 1000 that is sealed at distal end 1220, and in fluid communication with opening 1105. Opening 1105 is in fluid communication with a gas supply/vacuum apparatus 1135 via a pressure regulator 1145 (e.g., a valve). As the pressure in chamber 2000 is reduced during evacuation, pressure regulator 1145 opens to allow apparatus 1135 to reduce the pressure (e.g., by pumping out gas) in the portion of endoscope 1000 that is sealed at distal end 1220 so that the pressure differential between the exterior of endoscope 1000 and the portion of endoscope 1000 that is sealed at distal end 1220 is relatively small (e.g., less than about five psi, less than about four psi, less than about three psi, less than about two psi, less than about one psi, less than 0.5 psi, less than 0.2 psi) during evacuation. After evacuation, as the pressure in chamber 2000 is increased, pressure regulator 1145 opens to allow apparatus 1135 to increase the pressure (e.g., by pumping in gas) in the portion of endoscope 1000 that is sealed at distal end 1220 so that the pressure differential between the exterior of endoscope 1000 and the portion of endoscope 1000 that is sealed at distal end 1220 is relatively small (e.g., less than about five psi, less than about four psi, less than about three psi, less than about two psi, less than about one psi, less than 0.5 psi, less than 0.2 psi) during pressurization. In general, pressure regulator 1145 can be manually controlled, automated, or both. In certain embodiments, pressure regulator 1145 can be varied continuously between a fully on position and a fully off position. In some embodiments, pressure regulator 1145 has only a fully on position and a fully off position.

In certain embodiments, pressure sensor 2700, temperature sensor 2800, and/or timer 2900 are used to determine whether the proper sterilization conditions (steam pressure, steam temperature, time that endoscope 1000 was exposed to the steam) were met (e.g., sterilization chamber 2000 operates under set sterilization conditions, and sensors 2700, 2800, and/or 2900 are used to verify that the conditions were met). In some embodiments, pressure sensor 2700, temperature sensor 2800 and/or timer 2900 can be used to monitor and adjust the steam pressure, steam temperature, and time of exposure (e.g., sensors 2700, 2800, and/or 2900 are used to control the conditions used during sterilization of endoscope 1000) to assist in sterilizing endoscope 1000 tinder appropriate conditions. Sensors 2700, 2800, and/or 2900 can be manually operated, automated, or both.

Updating Endoscope Status

After sterilizing endoscope 1000, the sterilization status and/or medical procedure enablement status of endoscope 1000 can be updated.

In some embodiments, sterilizing endoscope 1000 in a sterilizer automatically updates sterilization status of endoscope 1000 (e.g., as indicated by sterilization status indicator 1150) to indicate that endoscope 1000 has not been sterilized since last used in a medical procedure. As an example, indicator 1150 may change color (e.g., red to green) to indicate that endoscope 1000 has been sterilized since last used in a medical procedure. As another example, indicator 1150 may display a word (e.g., STERILIZED) to indicate that endoscope 1000 has been sterilized since last used in a medical procedure. As a further example, indicator 1150 may cover/not cover a marker on endoscope 1000 to indicate that endoscope 1000 has been sterilized since last used in a medical procedure. In some embodiments, the distal end of optical guide 1280 emits light when power source 1175 is turned on to indicate that endoscope 1000 has been sterilized since last used in a medical procedure. In certain embodiments, an articulation element functions properly to indicate that endoscope 1000 has been sterilized since last used in a medical procedure.

In certain embodiments, using the endoscope in a medical procedure automatically updates the medical procedure enablement status of endoscope 1000 (e.g., as indicated by indicator 1160) to indicate that endoscope 1000 is enabled for use in a medical procedure. As an example, indicator 1160 may change color (e.g., red to green) to indicate that endoscope 1000 is enabled for use in a medical procedure. As another example, indicator 1160 may display a word (e.g., ENABLED) to indicate that endoscope 1000 is enabled for use in a medical procedure. As a further example, indicator 1150 may cover/not cover a marker on endoscope 1000 to indicate that endoscope 1000 is enabled for use in a medical procedure. In some embodiments, the distal end of optical guide 1280 may emit light when power source 1175 is turned on to indicate that endoscope 1000 is enabled for use in a medical procedure. In certain embodiments, an articulation element functions properly to indicate that endoscope 1000 is enabled for use in a medical procedure.

Figure 14:
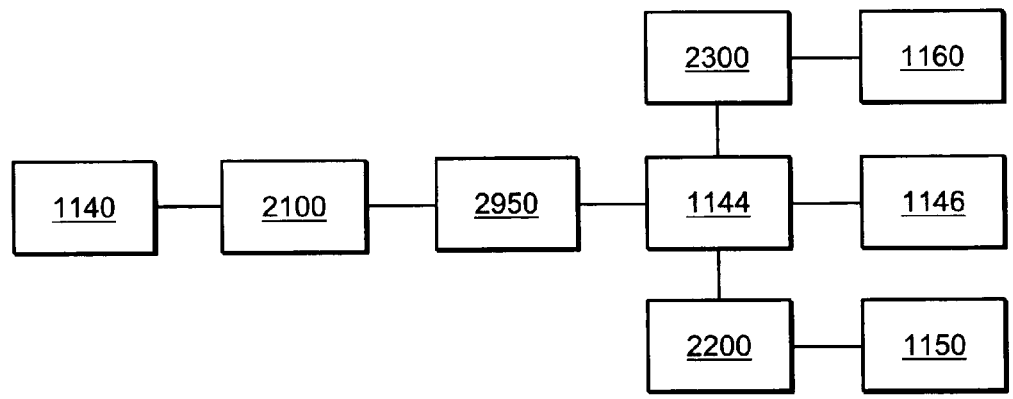
FIG. 14 is a schematic diagram of an embodiment of a system for reading an identity indicator.

In some embodiments, the sterilization status andior medical procedure enablement status of endoscope 1000 is updated using identity indicator 1140 (e.g., without updating sterilization status indicator 1150 and/or medical procedure enablement status indicator 1160). Referring to FIG. 14, identity sensor 2100 reads data from identity indicator 1140 (data corresponding to the identity of endoscope 1000), and passes the data to data processor 1144 via communication device 2950. Processor 1144 sends appropriate data to device 1146 to update data in the database contained on device 1146 for endoscope 1000 (e.g., to update data in the database for endoscope 1000 to indicate that endoscope 1000 has been sterilized since last used in a medical procedure). Processor 1144 may also instruct sterilization status adjustment device 2200 to update sterilization status indicator 1150 as appropriate (see discussion above), and/or processor 1144 may also instruct medical procedure enablement adjustment device 2300 to update medical procedure enablement adjustment status indicator 1160 as appropriate (see discussion above).

Endoscope Holder

Figure 15:
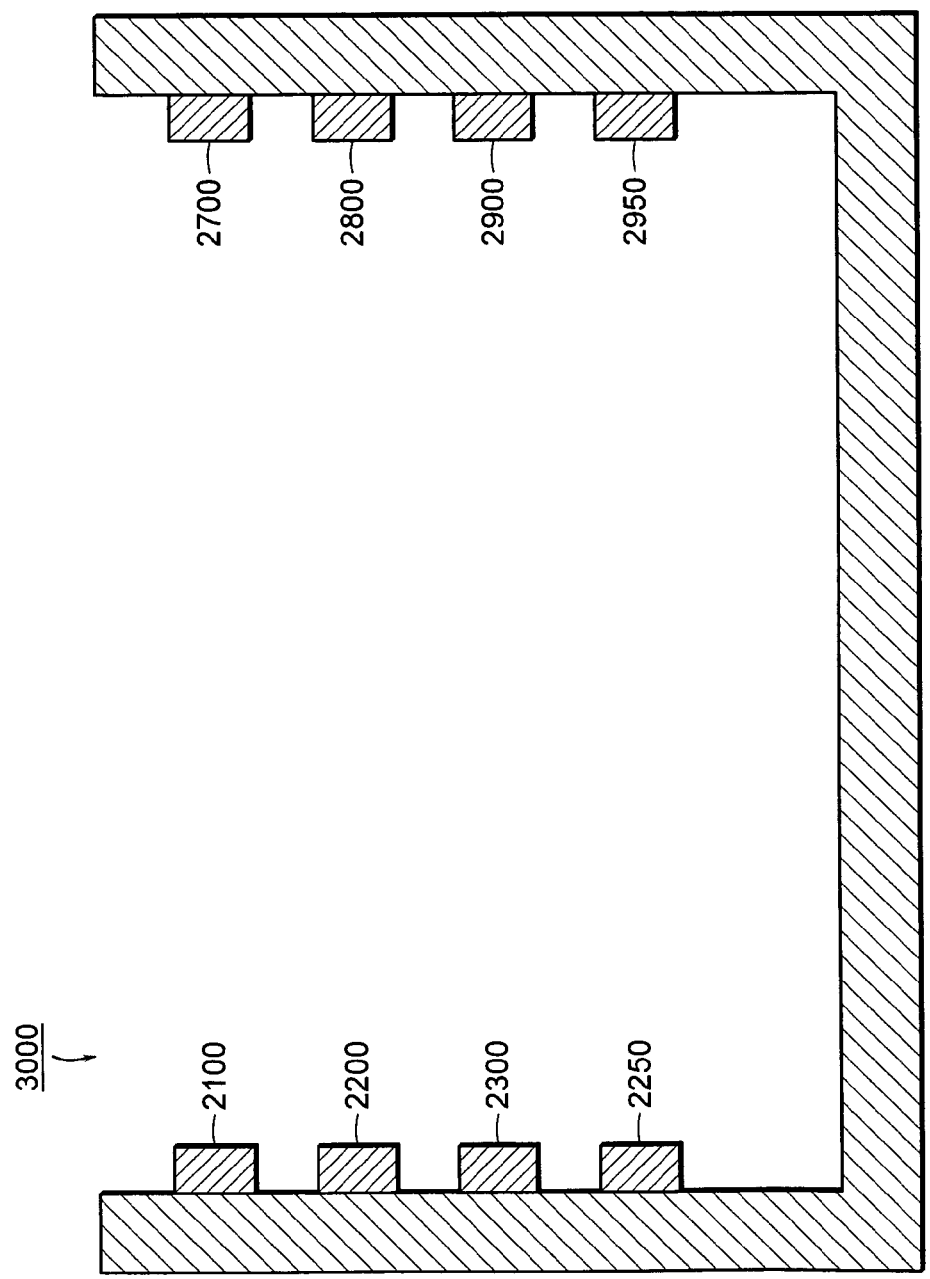
FIG. 15 is a cross-sectional view of an embodiment of an endoscope holder.

In certain embodiments sterilization chamber 2000 does not have identity sensor 2100, sterilization status adjustment device 2200, medical procedure enablement status adjustment device 2300, sterilization match sensor 2250, pressure sensor 2700, temperature sensor 2800, and/or timer 2900. In such embodiments, one or more of these components can be coupled to a device that can fit into sterilization chamber 2000 so that, while chamber 2000 itself does not have one or more of these components, the sterilization system still does have all these components disposed within chamber 2000 during sterilization. For example, FIG. 15 shows an endoscope holder 3000 (e.g., a tray) that can be repeatedly fit into sterilization chamber 2000, and that can be repeatedly removed from sterilization chamber 2000. Holder 3000 includes identity sensor 2100, sterilization status adjustment device 2200, medical procedure enablement status adjustment device 2300, sterilization match sensor 2250, pressure sensor 2700, temperature sensor 2800, and timer 2900.

Holder 3000 can be used as follows. Endoscope 1000 is placed in holder 3000, holder 3000 is placed in sterilization chamber 2000, and the match between endoscope 1000 and chamber 2000 is determined. If chamber 2000 and endoscope 1000 are not properly matched, chamber 2000 is shut down (see discussion above). Otherwise, the process continues. In some embodiments, holder 3000 and endoscope 1000 are configured so that cleaning devices 2400, 2500 and/or 2600 are appropriately positioned as tray 3000 is placed into chamber 2000. Sterilization chamber 2000 then goes through a sterilization cycle, sterilization conditions are checked, and the status of endoscope 1000 is updated (see discussion above). Each of sensor 2100, device 2200, device 2300, sensor 2250, sensor 2700, sensor 2800, sensor 2900, and/or transmitter 2950 can be integral with holder 3000, disposed in the interior of holder 3000, or disposed on the exterior of holder 3000.

Endoscope Holder Docking Station

Figure 16:
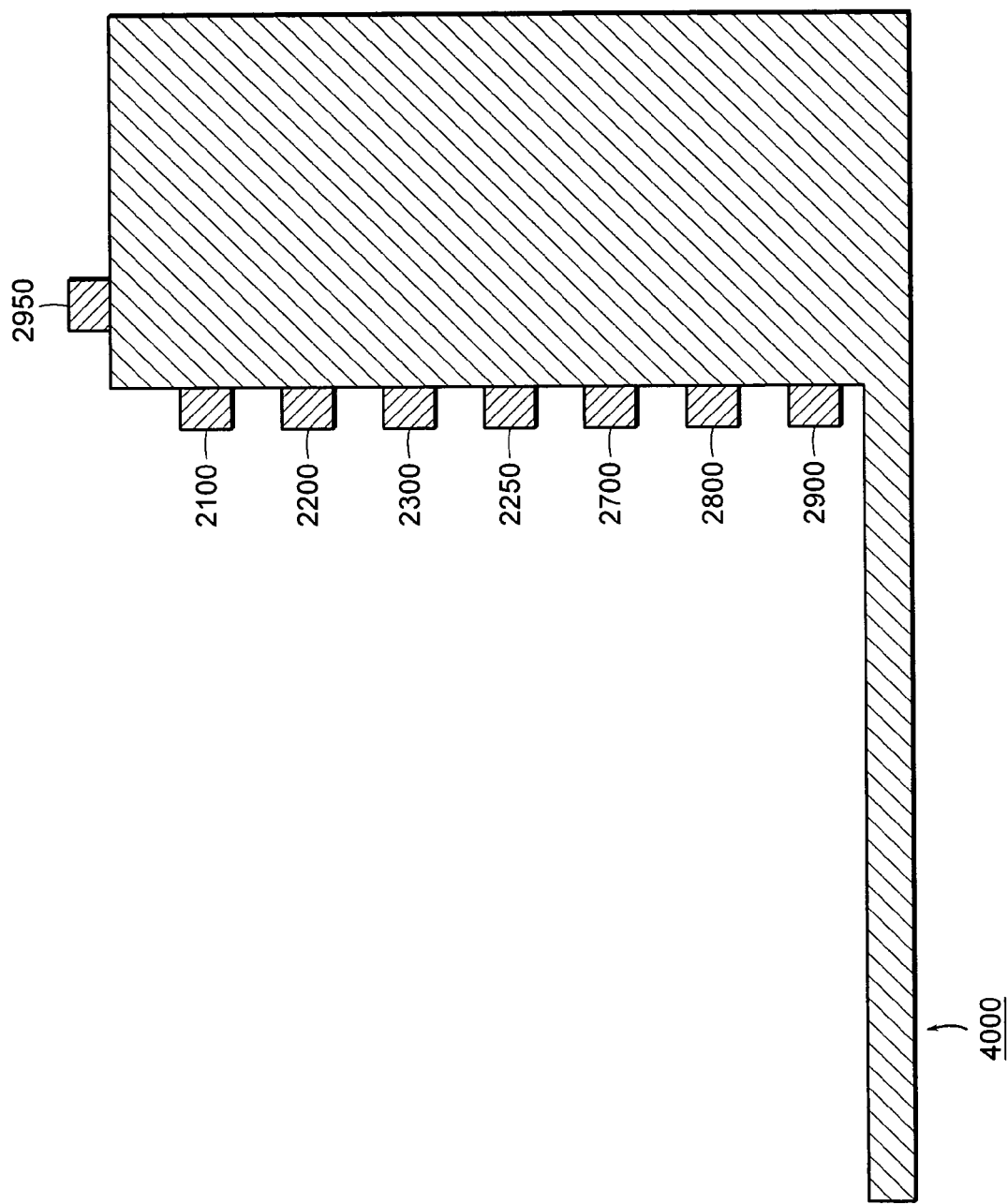
FIG. 16 is a cross-sectional view of an embodiment of a docking station for the endoscope holder of FIG. 15.

In some embodiments, holder 3000 does not include identity sensor 2100, sterilization status adjustment device 2200, medical procedure enablement status adjustment device 2300, sterilization match sensor 2250, pressure sensor 2700, temperature sensor 2800, and/or timer 2900. Referring to FIG. 16, in such embodiments, a docking station 4000 for holder 3000 can contain these components. Docking station 4000 can be used as follows. Holder 3000 is used as described above. After the sterilization cycle, holder 3000 is removed from chamber 2000 and connected to docking station 4000 (which may be remote from chamber 2000). The sterilization conditions are checked, and the status of endo scope 1000 is updated (see discussion above). Each of sensor 2100, device 2200, device 2300, sensor 2250, sensor 2700, sensor 2800, sensor 2900, and/or transmitter 2950 can be integral with docking station 4000, disposed in the interior of docking station 4000, or disposed on the exterior of docking station 4000. In some embodiments, docking station 4000 is configured to be electrically coupled, optically coupled and/or wirelessly coupled with holder 3000. In certain embodiments, docking station 4000 is configured to hold endoscope holder 3000 without such coupling with holder 3000.

Charging for Use of Endoscope

Figure 17:
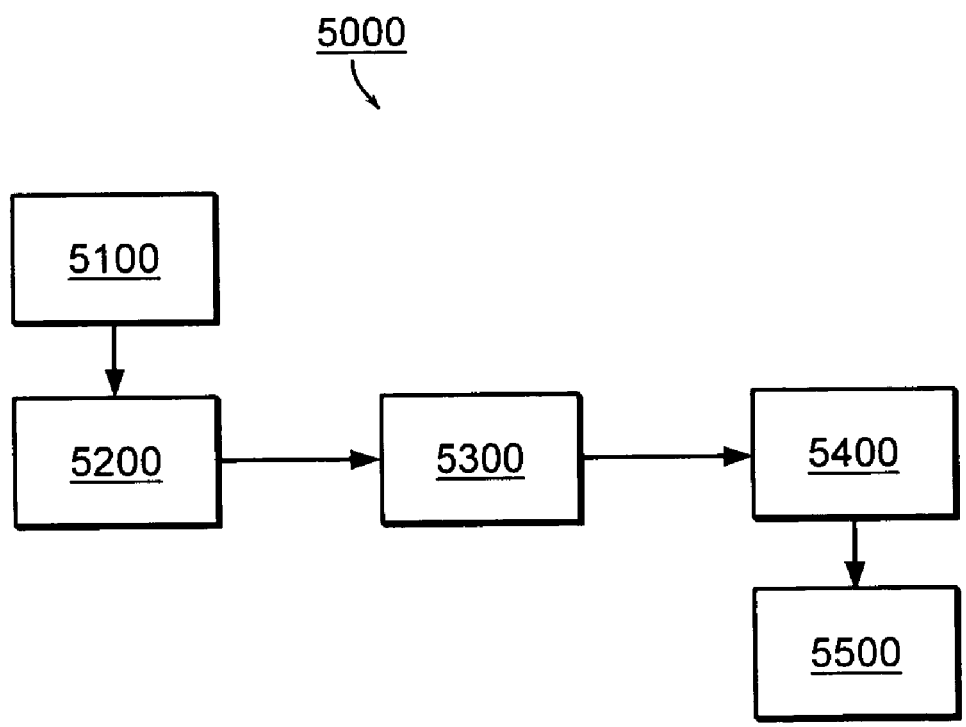
FIG. 17 is a flow chart for an embodiment of a method of charging a client for use of an endoscope.

FIG. 17 shows a flow chart for a method 5000 that can be used to charge a client for use of endoscope 1000. First, the client uses endoscope 1000 (5100), and this information is communicated to a data processor (5200). The data processor then communicates with a data storage device containing a database with data for endoscope 1000 (5300). The data processor uses the data for endoscope 1000 to calculate the client charge for using endoscope 1000 (5400). Depending on the type of account the client has, the data processor debits the account (e.g., by updating the database for endoscope 1000 contained on device 1446 to reduce the charge from the credit for the account) and forwards this information to the client, or the data processor bills the account (e.g., by updating the database for endoscope 1000 contained on device 1446 to indicate that the client has been sent a bill for the charge) and forwards the bill to the client (5500).

In general, this method can be performed as follows. The client uses endoscope 1000, and as data is communicated from endoscope 1000 to data processor 1144 and data storage device 1146 to update the data for endoscope 1000 in the database contained on device 1146 to indicate that the sterilization status and/or medical procedure enablement status of endoscope 1000 has changed, the database is updated to indicate that endoscope 1000 has undergone another use in a medical procedure. This can take place after use of endoscope 1000 (e.g., after use of endoscope 1000 but before cleaning of endoscope 1000, when endoscope 1000 is cleaned, when endoscope 1000 is matched with sterilization chamber 2000, after matching with sterilization chamber 2000 but before sterilization of endoscope 1000) and/or after sterilization of endoscope 1000 (e.g., after sterilization of endoscope 1000 but before the next use of endoscope 1000 in a medical procedure), but generally not both (see discussion above). During this process, processor 1144 recognizes that endoscope 1000 has undergone a use in a medical procedure, and processor 1144 communicates this to database 1146 (e.g., the database can contain information regarding the number of times endoscope 1000 has been used in a medical procedure). Processor 1144 then retrieves the appropriate data from the database to calculate the charge to the client, and processor 1144 retrieves appropriate data from the database to determine the type of account the client has (e.g., credited, noncredited) to determine how to charge the client. Processor 1144 then provides appropriate instructions so that the client is informed of the charge (e.g., by displaying the charge information on a video monitor so that a person can read this information and forward it to the client, by printing the information on a sheet that is forwarded to the client, by electronically/optically/wirelessly communicating this information to the client).

Various information can be contained in the database for endoscope 1000 that is stored on device 1146 and that is used by processor 1144 to determine the client charge for using endoscope 1000. In some embodiments, the information can include the identity of the client. For example, the client charge may depend upon whether the client is a private patient, a private doctor, a doctor who is part of a professional organization, a health maintenance organization, a private insurance company, or a government agency. In certain embodiments, the information can include the number of times the client has used endoscope 1000. For example, the rate per use may change (e.g., increase, decrease) as the number of uses increases. In some embodiments, the information can include the number of times that the client has used endoscope 1000 since the client was last billed. For example, the client can be billed based on a predetermined number of uses, as opposed to being billed on a per use basis. In certain embodiments, the information can include the total number of times that the client has used an endoscope in the system. For example, the client may be associated with multiple endoscopes through an account, and the total number of uses for the multiple endoscopes can be stored in the database so that the client charge per endoscope use can change (e.g., increase, decrease) as the total number of endoscope uses increases. In some embodiments, the information can include the total number of times that the client has used a sterilization chamber in the system. For example, the client may have access to multiple sterilization chambers, and the total number of sterilization chamber uses can be stored in the database so that the charge per use can change (e.g., increase, decrease) as the total number of sterilization system uses increases. In certain embodiments, the information can include the time of day that endoscope 1000 was used. For example, the charge per use can be lower if endoscope 1000 was used during off peak hours. In some embodiments, the information can include the frequency of use of endoscope 1000. For example, the charge per use can change (e.g., increase, decrease) as the number of uses per unit time increases.

In some embodiments, the client is charged before use of endoscope 1000 in a medical procedure (e.g., before each use, before each predetermined number of uses). In certain embodiments, the client is charged after use of endoscope 1000 in a medical procedure (e.g., after each use, after each predetermined number of uses).

While certain embodiments have been described, other embodiments are possible.

As an example, while the systems and methods have been described for use with endoscopes, other reusable medical instruments can be used in the systems and methods. A reusable medical instrument, as referred to herein, means a medical instrument that, after being used in a medical procedure, is treated (e.g., cleaned, disinfected, and/or sterilized) so that the device can be used again in a medical procedure. Examples of reusable medical instruments include laparoscopes, video imaging cameras and/or associated electronics, CCD imaging cameras and/or associated electronics, CMOS imaging cameras and/or associated electronics, wound closure devices (e.g., staplers, suturing devices), ultrasonic probes, umbilical cables, umbilicals for cutters, umbilicals for shavers, umbilicals for staplers, and endarterectomy devices.

As another example, while the above-described systems and methods have been described with respect to sterilization chambers and sterilization processes, more generally, the systems and methods can be used with any treatment that is used for a reusable medical instrument between uses of the instrument in a medical procedure. As an example, rather than a sterilization chamber and process, the systems and methods can use a disinfection chamber and process. In some embodiments, the treatment of the reusable medical instrument between uses in a medical procedure can include cleaning, disinfection and/or sterilization.

As a further example, the status checking and/or data updating for a reusable medical instrument can be done at any stage in the process that is desired. For example, the status of the reusable device can be checked and/or updated before use in a medical procedure, after the device is used in a medical procedure (e.g., between use in a medical procedure and treatment), and/or after the device is treated (e.g., sterilized and/or disinfected). In some embodiments, the status of the reusable medical instrument is checked and/or updated between use in a medical procedure and treatment, but not after treatment. In certain embodiments, the status of the reusable medical instrument is checked and/or updated after treatment, but not between use in a medical procedure and treatment. Similarly, data associated with the reusable medical instrument can be updated before the device is used in a medical procedure, after the device is used in a medical procedure (e.g., between use in a medical procedure and treatment), and/or after the device is treated.

While endoscopes having a light source in the manipulation portion have been described, endoscopes having one or more lights sources located in the elongated portion of the endoscope (e.g., at the distal end) can also be used. One or more of the light sources can be external to the endoscope (e.g., connected to the manipulation portion via an electrical connection, an optical connection, and/or a wireless connection).

While endoscopes having an internal power source have been described, endoscopes having an external power source (e.g., connected to the manipulation portion via an electrical connection, an optical connection, and/or a wireless connection) can be used.

While endoscopes having a wireless transmitter on the elongated portion have been described, endoscopes having an electrically connected and/or optically connected transmitter on the elongated portion can be used.

While endoscopes having a flexible portion 1215 have been described, in some embodiments region 1215 can be rigid or semi-rigid.

In some embodiments, the manipulation portion of an endoscope can have one or more oculars, one or more umbilicals, one or more connectors, and/or one or more valves. In embodiments in which the manipulation portion has an umbilical, the endoscope can be designed so that the cable automatically changes the status of the endoscope (e.g., sterilization status, medical procedure enablement status) when the umbilical is separated from the endoscope or is separated at its distal end (e.g., from the video processor, gas/vacuum/irrigation supply, and/or light source), and/or the umbilical can mechanically reset to indicate a change in status after use.

In certain embodiments, a light source can be formed of one or more LEDs (e.g., one or more red LEDs, one or more blue LEDs, one or more green LEDs, and/or one or more white LEDs).

In some embodiments, a medical instrument can have one or more joysticks that are used as control devices. Medical instruments containing such control devices are described, for example, in commonly owned and co-pending U.S. Provisional Patent Application Ser. No. 60/389,168, filed Jun. 17, 2002, and entitled "Mechanical Joystick Steering Mechanism for Borescope, Endoscope, Catheter, Guide Tube, and Working Tool," the contents of which are herby incorporated by reference.

In some embodiments, the systems can be used to provide methods of maintaining the condition of a reusable medical instrument. For example, the database can maintain a record of the number of times the reusable medical instrument has been used in a medical procedure since it last underwent a maintenance procedure. The data processor can retrieve this information from the database, and, when the database indicates that the reusable medical instrument has undergone the predetermined number of uses since last undergoing a maintenance procedure, the processor can disable the reusable medical instrument from use in a medical procedure. The database can then instruct the client that the reusable medical instrument has been disabled.

In certain embodiments, the systems can be used to provide methods of maintaining supplies associated with uses of a reusable medical instrument (e.g., cytology brushes, baskets, snares, graspers, forceps). For example, the database can maintain a record of the number of times the reusable medical instrument has been used in a medical procedure since the client associated with the instrument was provided supplies for the instrument. The data processor can retrieve this information from the database, and, when the database indicates that the reusable medical instrument has undergone the predetermined number of uses since the client was last provided the supplies, the processor can instruct a medical procedure enablement status adjustment device for the instrument to disable the reusable medical instrument from use in a medical procedure. The database can then instruct the client that the reusable medical instrument has been disabled. In some embodiments, a user or handler of the instrument can provide the data processor with information regarding the medical procedure that is intended to be used with the instrument, and the data processor can interact with the database to determine whether sufficient supplies are available for the instrument to be used in the particular procedure.

While reusable medical instruments and medical procedures have been described, other instruments and procedures can also be used. For example, the instruments can be designed to be reusable for industrial uses (e.g., for inspecting the interior of an aircraft engine), and the procedures can be industrial procedures (e.g., inspecting the interior of an aircraft engine).

While the pressure regulator and gas/vacuum source have been described as being coupled to a treatment chamber (e.g., a sterilization chamber), other embodiments can be used. For example, the pressure regulator and/or gas/vacuum source can be coupled to a holder (e.g., a tray) for the reusable instrument (e.g., a reusable medical instrument, such as an endoscope).

Other embodiments are in the claims.

The invention claimed is:

1. A method of sterilizing an endoscope, the endoscope comprising a flexible elongated portion having an exterior and a sealed interior, the method comprising:
   a) sealing the endoscope within a sterilization chamber;
   b) evacuating the sterilization chamber;
   c) actively pumping gas out of the sealed interior of the endoscope during step b) to regulate a pressure differential between the exterior and the scaled interior of the endoscope;
   d) increasing the pressure within the chamber, and
   e) actively pumping gas into the sealed interior of the endoscope during step d) to regulate a pressure differential between the exterior and the sealed interior of the endoscope;
   wherein the interior of the endoscope remains sealed from the sterilization chamber.

2. The method of claim 1, further comprising determining the pressure differential between the interior and the exterior of the endoscope during evacuation of the sterilization chamber.

3. The method of claim 2, wherein said pressure differential is regulated to be at most about five psi.

4. The method of claim 1, further comprising determining the pressure differential between the interior and the exterior of the endoscope during step d).

5. The method of claim 4, wherein said pressure differential is regulated to be at most about five psi.

6. The method of claim 1, wherein the pressure within the sterilization chamber is increased by introducing steam into the chamber.

7. A method of sterilizing an endosoope, the endoscope comprising a flexible elongated portion having an exterior and a sealed interior, the method comprising:
   a) sealing the endoscope within a sterilization chamber;
   b) evacuating the sterilization chamber, while determining a pressure differential between the exterior and the sealed interior of the endoscope;
   c) actively pumping gas out of the interior of the endoscope to regulate the pressure differential;
   d) increasing the pressure within the chamber while determining a second pressure differential between the exterior and the sealed interior of the endoscope, and
   e) actively pumping gas into the interior of the endoscope to regulate the second pressure differential, wherein the interior of the endoscope remains sealed from the sterilization chamber.

8. The method of claim 7, wherein the pressure differential of c) is regulated to be at most about five psi.

9. The method of claim 7, wherein the second pressure differential is regulated to be at most about five psi.

10. The method of claim 7, wherein the pressure within the chamber is increased by introducing steam into the chamber.

* * * * *